United States Patent
Sakaguchi et al.

(10) Patent No.: US 11,858,984 B2
(45) Date of Patent: Jan. 2, 2024

(54) ANTI-S100A8/A9 ANTIBODY AND USE THEREOF

(71) Applicants: NATIONAL UNIVERSITY CORPORATION OKAYAMA UNIVERSITY, Okayama (JP); NIIGATA UNIVERSITY, Niigata (JP); NATIONAL UNIVERSITY CORPORATION GUNMA UNIVERSITY, Maebashi (JP); KAWASAKI GAKUENN EDUCATIONAL FOUNDATION, Kurashiki (JP)

(72) Inventors: Masakiyo Sakaguchi, Okayama (JP); Shinichi Toyooka, Okayama (JP); Shuta Tomida, Okayama (JP); Kazuhiko Shien, Okayama (JP); Hiroki Sato, Okayama (JP); Rie Kinoshita, Okayama (JP); Junichiro Futami, Okayama (JP); Kota Araki, Okayama (JP); Mikio Okazaki, Okayama (JP); Eisaku Kondo, Niigata (JP); Yusuke Inoue, Maebashi (JP); Akira Yamauchi, Kurashiki (JP)

(73) Assignees: National University Corporation Okayama University, Okayama (JP); Niigata University, Niigata (JP); National University Corporation Gunma University, Gunma (JP)

(*) Notice: Subject to any disclaimer, the term of this patent is extended or adjusted under 35 U.S.C. 154(b) by 0 days.

(21) Appl. No.: 17/050,384

(22) PCT Filed: Apr. 15, 2019

(86) PCT No.: PCT/JP2019/016100
§ 371 (c)(1),
(2) Date: Oct. 23, 2020

(87) PCT Pub. No.: WO2019/208290
PCT Pub. Date: Oct. 31, 2019

(65) Prior Publication Data
US 2021/0054061 A1 Feb. 25, 2021

(30) Foreign Application Priority Data
Apr. 27, 2018 (JP) ................. 2018-087576

(51) Int. Cl.
| | |
|---|---|
| *C07K 16/00* | (2006.01) |
| *C07K 16/46* | (2006.01) |
| *C07K 16/24* | (2006.01) |
| *A61P 11/00* | (2006.01) |
| *A61P 35/04* | (2006.01) |
| *A61K 39/00* | (2006.01) |

(52) U.S. Cl.
CPC .............. *C07K 16/24* (2013.01); *A61P 11/00* (2018.01); *A61P 35/04* (2018.01); *A61K 2039/505* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,659,087 B2 * | 2/2010 | Colgin | G01N 33/6893 435/7.1 |
| 2007/0249003 A1 | 10/2007 | Colgin et al. | |
| 2011/0212104 A1 | 9/2011 | Beaumont et al. | |
| 2015/0210768 A1 | 7/2015 | Roth | |
| 2023/0144545 A1 | 5/2023 | Sakaguchi et al. | |

FOREIGN PATENT DOCUMENTS

| | | |
|---|---|---|
| CN | 102985113 | 3/2013 |
| JP | 2012507723 A | 3/2012 |
| JP | 2015-533485 | 11/2015 |
| WO | WO 2011/106297 A2 | 9/2011 |

(Continued)

OTHER PUBLICATIONS

Ikemoto et al. New ELISA System for Myeloid-related Protein Complex (MRP8/14) and Its Clinical Significance as a Sensitive Marker for Inflammatory Responses Associated with Transplant Rejection. Clinical Chemistry 49:4 49:4, 594-600 (2003) (Year: 2003).*

Ikemoto et al. Intrinsic function of S100A8/A9 complex as an anti-inflammatory protein in liver injury induced by lipopolysaccharide in rats. Iinica Chimica Acta 376 (2007) 197-204 (Year: 2007).*

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

(Continued)

*Primary Examiner* — Maher M Haddad
(74) *Attorney, Agent, or Firm* — Don D. Cha; HDC Intellectual Property Law, LLP

(57) ABSTRACT

Provided is a substance capable of effectively suppressing cancer metastasis or a pharmaceutical composition that effectively acts on an inflammatory disease. The pharmaceutical composition is a pharmaceutical composition containing, as an active ingredient, an antibody or an antibody fragment thereof having antigen-binding activity for an S100A8/A9 heterodimer, and blocks interaction between S100A8/A9 and a group of receptors therefor, to thereby strongly suppress cancer metastasis both in vitro and in vivo, or alleviate inflammation. That is, the anti-S100A8/A9 antibody or the antibody fragment thereof can strongly suppress cancer metastasis or alleviate inflammation, by virtue of its blocking action on the interaction between S100A8/A9 and the group of receptors therefor.

20 Claims, 17 Drawing Sheets

Specification includes a Sequence Listing.

(56) References Cited

FOREIGN PATENT DOCUMENTS

WO  WO 2014/037588 A1  3/2014
WO  WO 2017/045070 A1  3/2017

OTHER PUBLICATIONS

Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Mahnke et al. Heterodimers of the calcium-binding proteins MRP8 and MRP14 are expressed on the surface of human monocytes upon adherence to fibronectin and collagen. Relation to TNF-α, IL-6, and superoxide production. J. Leukoc. Biol. 57: 63-71; 1995 (Year: 1995).*
Hessian and Fisher. The heterodimeric complex of MRP-8 (S100A8) and MRP-14 (S100A9) Antibody recognition, epitope definition and the implications for structure. Eur. J. Biochem. 268, 353-363 (2001). (Year: 2001).*
Wang et al. S100A8/A9 in Inflammation. Front. Immunol. 9:1298, pp. 1-14 (2018) (Year: 2018).*
Soulas et al. Recently Infiltrating MAC387+ Monocytes/ Macrophages. A Third Macrophage Population Involved in SIV and HIV Encephalitic Lesion Formation. Am J Pathol. May 2011; 178(5):2121-35. (Year: 2011).*
Hiratsuka Sachie et al., Nature Cell Biology, 2006, vol. 8(12), pp. 1369-1375.
Rie Kinoshita et al., Int. J. Cancer, 2019, vol. 145(2), pp. 569-575.
Araki Kota et al., J. Mol. Med., 2020, vol. 99(1), pp. 131-145.
P A Hessin et al., Eur. J. Biochem., 2001, vol. 268(2), pp. 353-363.
Rudikoff S. et al., PNAS, 1982, vol. 79(1), pp. 1979-1983.
Machine Translation of The Notice of Reasons for Refusal, dated Mar. 28, 2023, for the corresponding Japanese Patent Application No. 2020-516238.
Machine Translation of the First Review of the Opinion Notification, dated Apr. 27, 2023.

* cited by examiner

ANALYSIS OF S100A8/A9 BY GEL FILTRATION HPLC

STABILITIES OF S100A8A9 HETERODIMER AND RESPECTIVE HOMODIMERS OF A8 AND A9

Co-folding heterodimerization of S100A8/A9

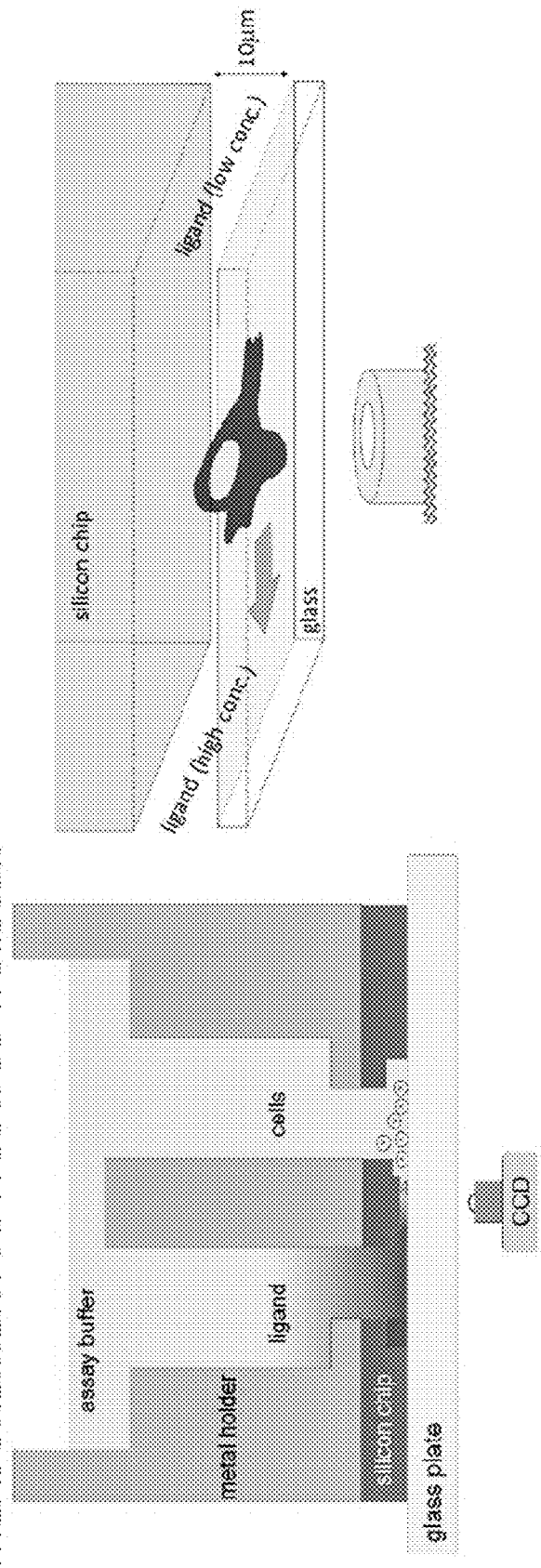
Fig. 7  EVALUATION WITH MINUTE CELL CHEMOTAXIS MEASUREMENT APPARATUS TAXiScan

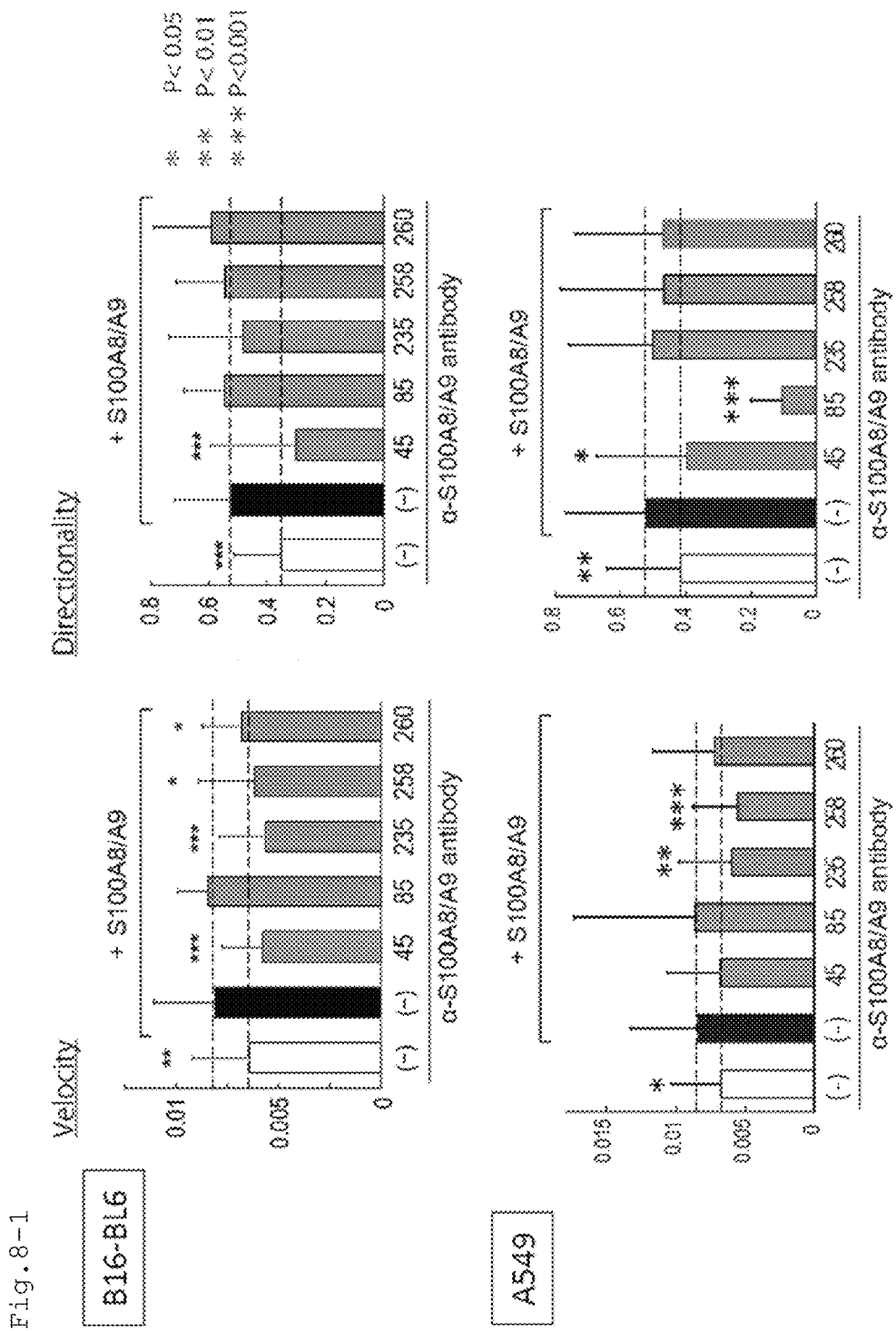

Fig.19
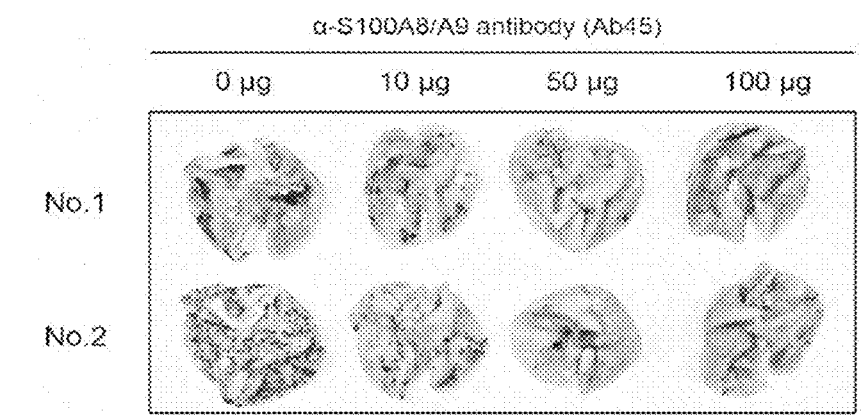
Fig.20
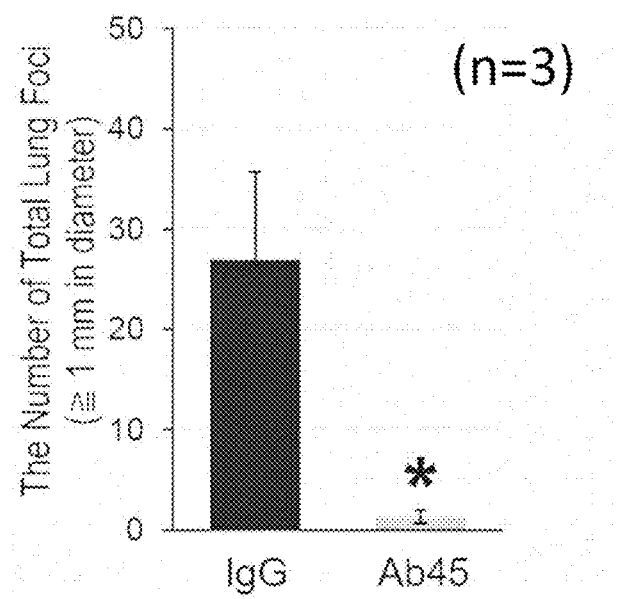
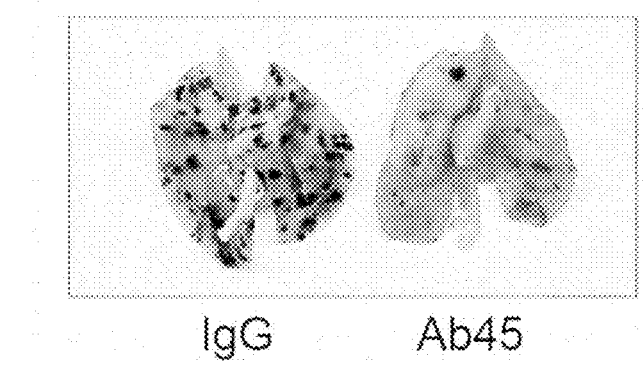

S100 A8          S100 A9

[UPPER] EXAMPLE OF BLEOMYCIN INJECTION

[LOWER] EXAMPLE OF BLEOMYCIN+ANTI-S100A8/A9 ANTIBODY TREATMENT (FIBROSIS IS REMARKABLY SUPPRESSED)

ANTI-S100A8/A9 ANTIBODY AND USE THEREOF

CROSS-REFERENCE TO RELATED APPLICATIONS

This application is a 35 U.S.C. § 371 of PCT Patent Application No. PCT/JP2019/016100, filed Apr. 15, 2019, which claims the priority benefit of Japanese Patent Application No. 2018-087576, filed Apr. 27, 2018, all of which are incorporated herein by reference in their entirety.

TECHNICAL FIELD

The present invention relates to an antibody or an antibody fragment thereof having antigen-binding activity for a heterodimer of S100A8 and S100A9 (hereinafter sometimes referred to as "S100A8/A9 heterodimer"). More specifically, the present invention relates to an antibody or an antibody fragment thereof that undergoes an antigen-antibody reaction with the S100A8/A9 heterodimer, or with the S100A8/A9 heterodimer and an S100A8 monomer or an S100A9 monomer. The present invention also relates to a pharmaceutical composition containing the antibody or the antibody fragment thereof as an active ingredient.

The present application claims priority from Japanese Patent Application No. 2018-87576, which is incorporated herein by reference.

BACKGROUND ART

Control of metastasis of a malignant tumor is a key issue directly linked to overcoming of cancer. However, there have not yet been many instances of development of therapeutic drugs from the viewpoint of controlling metastasis.

S100 proteins are each a calcium-binding protein that is expressed in a cell-type-specific manner and has two EF-hands, and 20 kinds of subfamilies thereof have been recognized heretofore. S100A8 (MRP8, calgranulin A) is a member of the calcium-binding protein S100 family, and is usually coexpressed with S100A9 (MRP14, calgranulin B). An S100A8/A9 complex (calprotectin) is considered to accumulate in body fluid during inflammation, thereby being involved in the onset of a human chronic inflammatory disease, such as rheumatoid arthritis (RA), cystic fibrosis, Crohn's disease, ulcerative colitis, allergic dermatitis, or an infection.

The S100A8/A9 complex is, for example, secreted by the lungs, and has a function of attracting distant cancer cells and a function of forming, in the lungs, an immune-suppressive environment appropriate for settlement and proliferation of cancer cells. It has been reported that a relationship between the S100A8/A9 complex (soil signal) emitted by an organ and an S100A8/A9 receptor group (soil sensor) on the cancer cell side is important for a cancer metastasis control mechanism, and that receptors for S100A8/A9 have been discovered (Non Patent Literatures 1 to 4). As the group of receptors for S100A8/A9, there are known, for example, EMMPRIN, neuroplastin-α (NPTNα), NPTNβ, M-cell adhesion molecule (MCAM), and ALCAM. Those receptors are expressed on the cancer cell side, and have a function of catching an S100A8/A9 signal to drive cancer cells to metastasize.

There is a report of a screening method for a chronic inflammation suppressor or a cancer metastasis suppressor based on binding inhibition with a focus on EMMPRIN among the receptors for S100A8/A9 (Patent Literature 1). In Patent Literature 1, it is shown that EMMPRIN is a receptor particularly for S100A9, and there is a disclosure that results of screening have found Japanese mugwort extract, dong quai extract, white dead-nettle extract, and the like to inhibit binding between EMMPRIN and S100A9. There is a report of a screening method for a cell proliferation suppressor based on binding inhibition with a focus on NPTN among the receptors for S100A8/A9 (Patent Literature 2). In Patent Literature 2, there is a disclosure that results of screening have found Japanese mugwort extract, glycyrrhiza extract, ginseng extract, and the like to inhibit binding between NPTN and S100A8. Compounds regarded as S100-inhibitors have been reported to be useful for treatment of, for example, cancer, autoimmune diseases, inflammatory diseases and neurodegenerative diseases (Patent Literature 3). In addition, there is also a report of usefulness of S100A9 as a biomarker for inflammatory bowel disease (Patent Literature 4).

S100A9 polyclonal antibodies have been reported to be useful as an imaging agent for an organ in an immunosuppressive state to which cancer metastasizes (Non Patent Literature 5), and also to suppress migration of breast cancer cells in an in vitro experiment (Non Patent Literature 6). Further, there is also a report that S100A8 polyclonal antibodies, or a combination of S100A8 polyclonal antibodies and S100A9 polyclonal antibodies suppressed migration of cancer cells injected via the tail vein to the lungs in an in vivo experiment using mice (Non Patent Literature 7). As described above, the S100 family is associated with cancer metastasis and the like, and suppression of binding between S100A8 and/or S100A9 and receptors therefor is presumed to suppress chronic inflammation and to suppress cancer metastasis. However, while the S100A8 polyclonal antibodies and S100A9 polyclonal antibodies used in Non Patent Literatures 5 to 7 described above were generated using S100A8 and S100A9 as antigens, respectively, their reactivity (antigen-binding activity) with an S100A8/A9 heterodimer is totally unknown.

In Non Patent Literature 8, there is a disclosure that the S100A8/A9 heterodimer was generated and purified. There is a demand for development of a medicament capable of more effectively suppressing metastasis of a malignant tumor.

CITATION LIST

Patent Literature

[PTL 1] JP 2011-47932 A
[PTL 2] JP 2014-59210 A
[PTL 3] WO 2015/177367 A1
[PTL 4] JP 2016-217956 A

Non Patent Literature

[NPL 1] Sumardika I W. et al., Oncol Res. 2017 Sep. 18. doi: 10.3727/096504017X15031557924123.
[NPL 2] Sakaguchi M. et al., J Invest Dermatol., 136(11): 2240-2250, (2016).
[NPL 3] Ruma I M. et al., Clin Exp Metastasis., 33(6): 609-27, (2016).
[NPL 4] Hibino T. et al., Cancer Res., 1; 73(1): 172-83, (2013).
[NPL 5] Eisenblaetter M. et al., Theranostics., 15; 7(9): 2392-2401, (2017).
[NPL 6] Yan Liu. et al., Neuro-Oncology, 15(7): 891. 903, (2013).

[NPL 7] Hiratsuka S. et al., Nat Cell Biol., 8(12): 1369-75, (2006).
[NPL 8] Futami J. et al., Biochem Biophys Rep., 19; 6: 94-100, (2016).

SUMMARY OF INVENTION

Technical Problem

An object of the present invention is to provide a substance capable of effectively suppressing cancer metastasis or a pharmaceutical composition useful against an inflammatory disease. Specifically, the object is to provide a pharmaceutical composition containing, as an active ingredient, an antibody or an antibody fragment thereof having antigen-binding activity for an S100A8/A9 heterodimer.

Solution to Problem

In order to achieve the above-mentioned object, the inventors of the present invention have made extensive investigations with a focus on S100A8 and S100A9 (hereinafter sometimes abbreviated as "S100A8/A9") and a group of receptors therefor (EMMPRIN, NPTNβ, MCAM, and ALCAM), and as a result, have recognized that the blocking of interaction between S100A8/A9 and the group of receptors therefor strongly suppresses cancer metastasis both in vitro and in vivo, or alleviates inflammation. Thus, the inventors have completed the present invention. In the present invention, it has been found for the first time that, as compared to S100A8 polyclonal antibodies and S100A9 polyclonal antibodies generated using S100A8 and S100A9 as antigens, respectively, an antibody generated using an S100A8/A9 heterodimer as an antigen has an action of most effectively blocking the interaction between S100A8/A9 and the group of receptors therefor.

That is, the present invention includes the following.

1. A pharmaceutical composition, including an antibody or an antibody fragment thereof as an active ingredient, the antibody or the antibody fragment thereof having antigen-binding activity for a heterodimer of S100A8 and S100A9.

2. The pharmaceutical composition according to the above-mentioned item 1, wherein the antibody or the antibody fragment thereof has a neutralizing ability against any one selected from the following items (i) to (iii):
   (i) the heterodimer of S100A8 and S100A9;
   (ii) the heterodimer of S100A8 and S100A9, and an S100A8 monomer; and
   (iii) the heterodimer of S100A8 and S100A9, and an S100A9 monomer.

3. The pharmaceutical composition according to the above-mentioned item 1 or 2, wherein the antibody or the antibody fragment thereof is a monoclonal antibody.

4. The pharmaceutical composition according to the above-mentioned item 3, wherein a subclass of the monoclonal antibody is any one selected from $IgG_1$, $IgG_2$, $IgG_3$, and $IgG_4$.

5. The pharmaceutical composition according to any one of the above-mentioned items 1 to 4,
   wherein the antibody or the antibody fragment thereof as the active ingredient is an antibody containing: heavy chain variable regions including a heavy chain variable region 1 (CDR H1), a heavy chain variable region 2 (CDR H2), and a heavy chain variable region 3 (CDR H3); and light chain variable regions including a light chain variable region 1 (CDR L1), a light chain variable region 2 (CDR L2), and a light chain variable region 3 (CDR L3),
   wherein the heavy chain variable region 1 (CDR H1) contains any one of the amino acid sequences set forth in SEQ ID NO: 7, SEQ ID NO: 10, SEQ ID NO: 13, SEQ ID NO: 16, or SEQ ID NO: 19, or the amino acid sequence having one or a plurality of amino acids deleted, added, substituted, or inserted in SEQ ID NO: 7, 10, 13, 16, or 19,
   wherein the heavy chain variable region 2 (CDR H2) contains any one of the amino acid sequences set forth in SEQ ID NO: 8, SEQ ID NO: 11, SEQ ID NO: 14, SEQ ID NO: 17, or SEQ ID NO: 20, or the amino acid sequence having one or a plurality of amino acids deleted, added, substituted, or inserted in SEQ ID NO: 8, 11, 14, 17, or 20,
   wherein the heavy chain variable region 3 (CDR H3) contains any one of the amino acid sequences set forth in SEQ ID NO: 9, SEQ ID NO: 12, SEQ ID NO: 15, SEQ ID NO: 18, or SEQ ID NO: 21, or the amino acid sequence having one or a plurality of amino acids deleted, added, substituted, or inserted in SEQ ID NO: 9, 12, 15, 18, or 21,
   wherein the light chain variable region 1 (CDR L1) contains any one of the amino acid sequences set forth in SEQ ID NO: 22, SEQ ID NO: 25, SEQ ID NO: 28, SEQ ID NO: 31, or SEQ ID NO: 34, or the amino acid sequence having one or a plurality of amino acids deleted, added, substituted, or inserted in SEQ ID NO: 22, 25, 28, 31, or 34,
   wherein the light chain variable region 2 (CDR L2) contains any one of the amino acid sequences set forth in SEQ ID NO: 23, SEQ ID NO: 26, SEQ ID NO: 29, SEQ ID NO: 32, or SEQ ID NO: 35, or the amino acid sequence having one or a plurality of amino acids deleted, added, substituted, or inserted in SEQ ID NO: 23, 26, 29, 32, or 35, and
   wherein the light chain variable region 3 (CDR L3) contains any one of the amino acid sequences set forth in SEQ ID NO: 24, SEQ ID NO: 27, SEQ ID NO: 30, SEQ ID NO: 33, or SEQ ID NO: 36, or the amino acid sequence having one or a plurality of amino acids deleted, added, substituted, or inserted in SEQ ID NO: 24, 27, 30, 33, or 36.

6. The pharmaceutical composition according to the above-mentioned item 5,
   wherein the heavy chain variable region 1 (CDR H1) contains any one of the amino acid sequences set forth in SEQ ID NO: 7, or the amino acid sequence having one or a plurality of amino acids deleted, added, substituted, or inserted in the amino acid sequence set forth in SEQ ID NO: 7,
   wherein the heavy chain variable region 2 (CDR H2) contains any one of the amino acid sequences set forth in SEQ ID NO: 8, or the amino acid sequence having one or a plurality of amino acids deleted, added, substituted, or inserted in the amino acid sequence set forth in SEQ ID NO: 8,
   wherein the heavy chain variable region 3 (CDR H3) contains any one of the amino acid sequences set forth in SEQ ID NO: 9, or the amino acid sequence having one or a plurality of amino acids deleted, added, substituted, or inserted in the amino acid sequence set forth in SEQ ID NO: 9,
   wherein the light chain variable region 1 (CDR L1) contains any one of the amino acid sequences set forth in SEQ ID NO: 22, or the amino acid sequence having one or a plurality of amino acids deleted, added, substituted, or inserted in the amino acid sequence set forth in SEQ ID NO: 22, wherein the light chain variable region 2 (CDR L2) contains any one of the amino acid sequences set forth in SEQ ID NO: 23, or the amino acid sequence having one or a plurality of amino acids deleted, added, substituted, or inserted in the amino acid sequence set forth in SEQ ID NO: 23, and wherein the light chain variable region 3 (CDR L3) contains any one of the amino acid sequences set forth in SEQ ID NO: 24, or the amino acid sequence having one or a plurality of amino acids deleted, added, substituted, or inserted in the amino acid sequence set forth in SEQ ID NO: 24.

7. The pharmaceutical composition according to the above-mentioned item 5, wherein the heavy chain variable region 1 (CDR H1) contains any one of the amino acid sequences set forth in SEQ ID NO: 10, or the amino acid sequence having one or a plurality of amino acids deleted, added, substituted, or inserted in the amino acid sequence set forth in SEQ ID NO: 10, wherein the heavy chain variable region 2 (CDR H2) contains any one of the amino acid sequences set forth in SEQ ID NO: 11, or the amino acid sequence having one or a plurality of amino acids deleted, added, substituted, or inserted in the amino acid sequence set forth in SEQ ID NO: 11, wherein the heavy chain variable region 3 (CDR H3) contains any one of the amino acid sequences set forth in SEQ ID NO: 12, or the amino acid sequence having one or a plurality of amino acids deleted, added, substituted, or inserted in the amino acid sequence set forth in SEQ ID NO: 12, wherein the light chain variable region 1 (CDR L1) contains any one of the amino acid sequences set forth in SEQ ID NO: 25, or the amino acid sequence having one or a plurality of amino acids deleted, added, substituted, or inserted in the amino acid sequence set forth in SEQ ID NO: 25, wherein the light chain variable region 2 (CDR L2) contains any one of the amino acid sequences set forth in SEQ ID NO: 26, or the amino acid sequence having one or a plurality of amino acids deleted, added, substituted, or inserted in the amino acid sequence set forth in SEQ ID NO: 26, and wherein the light chain variable region 3 (CDR L3) contains any one of the amino acid sequences set forth in SEQ ID NO: 27, or the amino acid sequence having one or a plurality of amino acids deleted, added, substituted, or inserted in the amino acid sequence set forth in SEQ ID NO: 27.

8. The pharmaceutical composition according to the above-mentioned item 5, wherein the heavy chain variable region 1 (CDR H1) contains any one of the amino acid sequences set forth in SEQ ID NO: 13, or the amino acid sequence having one or a plurality of amino acids deleted, added, substituted, or inserted in the amino acid sequence set forth in SEQ ID NO: 13, wherein the heavy chain variable region 2 (CDR H2) contains any one of the amino acid sequences set forth in SEQ ID NO: 14, or the amino acid sequence having one or a plurality of amino acids deleted, added, substituted, or inserted in the amino acid sequence set forth in SEQ ID NO: 14, wherein the heavy chain variable region 3 (CDR H3) contains any one of the amino acid sequences set forth in SEQ ID NO: 15, or the amino acid sequence having one or a plurality of amino acids deleted, added, substituted, or inserted in the amino acid sequence set forth in SEQ ID NO: 15, wherein the light chain variable region 1 (CDR L1) contains any one of the amino acid sequences set forth in SEQ ID NO: 28, or the amino acid sequence having one or a plurality of amino acids deleted, added, substituted, or inserted in the amino acid sequence set forth in SEQ ID NO: 28, wherein the light chain variable region 2 (CDR L2) contains any one of the amino acid sequences set forth in SEQ ID NO: 29, or the amino acid sequence having one or a plurality of amino acids deleted, added, substituted, or inserted in the amino acid sequence set forth in SEQ ID NO: 29, and wherein the light chain variable region 3 (CDR L3) contains any one of the amino acid sequences set forth in SEQ ID NO: 30, or the amino acid sequence having one or a plurality of amino acids deleted, added, substituted, or inserted in the amino acid sequence set forth in SEQ ID NO: 30.

9. The pharmaceutical composition according to the above-mentioned item 5, wherein the heavy chain variable region 1 (CDR H1) contains any one of the amino acid sequences set forth in SEQ ID NO: 16, or the amino acid sequence having one or a plurality of amino acids deleted, added, substituted, or inserted in the amino acid sequence set forth in SEQ ID NO: 16, wherein the heavy chain variable region 2 (CDR H2) contains any one of the amino acid sequences set forth in SEQ ID NO: 17, or the amino acid sequence having one or a plurality of amino acids deleted, added, substituted, or inserted in the amino acid sequence set forth in SEQ ID NO: 17, wherein the heavy chain variable region 3 (CDR H3) contains any one of the amino acid sequences set forth in SEQ ID NO: 18, or the amino acid sequence having one or a plurality of amino acids deleted, added, substituted, or inserted in the amino acid sequence set forth in SEQ ID NO: 18, wherein the light chain variable region 1 (CDR L1) contains any one of the amino acid sequences set forth in SEQ ID NO: 31, or the amino acid sequence having one or a plurality of amino acids deleted, added, substituted, or inserted in the amino acid sequence set forth in SEQ ID NO: 31, wherein the light chain variable region 2 (CDR L2) contains any one of the amino acid sequences set forth in SEQ ID NO: 32, or the amino acid sequence having one or a plurality of amino acids deleted, added, substituted, or inserted in the amino acid sequence set forth in SEQ ID NO: 32, and wherein the light chain variable region 3 (CDR L3) contains any one of the amino acid sequences set forth in SEQ ID NO: 33, or the amino acid sequence having one or a plurality of amino acids deleted, added, substituted, or inserted in the amino acid sequence set forth in SEQ ID NO: 33.

10. The pharmaceutical composition according to the above-mentioned item 5, wherein the heavy chain variable region 1 (CDR H1) contains any one of the amino acid sequences set forth in SEQ ID NO: 19, or the amino acid sequence having one or a plurality of amino acids deleted, added, substituted, or inserted in the amino acid sequence set forth in SEQ ID NO: 19, wherein the heavy chain variable region 2 (CDR H2) contains any one of the amino acid sequences set forth in SEQ ID NO: 20, or the amino acid sequence having one or a plurality of amino acids deleted, added, substituted, or inserted in the amino acid sequence set forth in SEQ ID NO: 20, wherein the heavy chain variable region 3 (CDR H3) contains any one of the amino acid sequences set forth in SEQ ID NO: 21, or the amino acid sequence having one or a plurality of amino acids deleted, added, substituted, or inserted in the amino acid sequence set forth in SEQ ID NO: 21, wherein the light chain variable region 1 (CDR L1) contains any one of the amino acid sequences set forth in SEQ ID NO: 34, or the amino acid sequence having one or a plurality of amino acids deleted, added, substituted, or inserted in the amino acid sequence set forth in SEQ ID NO: 34, wherein the light chain variable region 2 (CDR L2) contains any one of the amino acid sequences set forth in SEQ ID NO: 35, or the amino acid sequence having one or a plurality of amino acids deleted, added, substituted, or inserted in the amino acid sequence set forth in SEQ ID NO: 35, and wherein the light chain variable region 3 (CDR L3) contains any one of the amino acid sequences set forth in SEQ ID NO: 36, or the amino acid sequence having one or a plurality of amino acids deleted, added, substituted, or inserted in the amino acid sequence set forth in SEQ ID NO: 36.

11. The pharmaceutical composition according to any one of the above-mentioned items 1 to 10, wherein the pharmaceutical composition is an anticancer agent or an anti-inflammatory agent.

12. The pharmaceutical composition according to the above-mentioned item 11, wherein the anticancer agent is a cancer metastasis suppressor and/or a cancer therapeutic agent.

13. The pharmaceutical composition according to the above-mentioned item 11 or 12, wherein cancer to be targeted by the anticancer agent is one kind or a plurality of kinds of cancers selected from skin cancer, lung cancer, stomach cancer, colon cancer, pancreatic cancer, liver cancer, lung cancer, kidney cancer, breast cancer, uterine cancer, bile duct cancer, esophageal cancer, pharyngeal cancer, biliary tract cancer, bladder cancer, blood cancer, lymphoma, ovarian cancer, prostate cancer, brain tumor, and thyroid cancer.

14. The pharmaceutical composition according to the above-mentioned item 11, wherein an inflammatory disease to be targeted by the anti-inflammatory agent is one kind or a plurality of kinds of inflammatory diseases selected from pulmonary fibrosis, lung injury (including acute lung injury and chronic lung injury), systemic inflammatory response syndrome, chronic obstructive pulmonary disease, elderly-onset rheumatoid arthritis, juvenile rheumatoid arthritis, juvenile idiopathic arthritis, inflammatory arthritis, reactive arthritis, uveitis-associated arthritis, inflammatory bowel disease-associated arthritis, inflammatory bowel disease, skin stress, insulitis, nephritis (including glomerulonephritis and pyelonephritis), cystic fibrosis, periodontitis, cervicitis, peritonitis, cancerous peritonitis, diabetic angiopathy, infectious disease, cardiovascular disease, autoimmune disease, autoinflammatory disease, pneumonia (including interstitial pneumonia and cryptogenic organizing pneumonia), pulmonary tuberculosis, pulmonary nontuberculous mycobacteriosis, pneumomycosis, pyothorax, endometritis, metritis, adnexitis, tubo-ovarian abscess, pelvic peritonitis, ankylosing spondylitis, psoriasis, psoriatic arthritis, esophagitis, gastroesophageal reflux disease, esophageal ulcer, gastric ulcer, duodenal ulcer, stress ulcer, steroid ulcer, acute gastritis, chronic gastritis, infectious enteritis, acute colitis, appendicitis, chronic enteritis, irritable bowel syndrome, ulcerative colitis, Crohn's disease, nonalcoholic steatohepatitis (NASH), ischemic colitis, acute pancreatitis, chronic pancreatitis, acute cholecystitis, chronic cholecystitis, cholangitis, hepatitis, collagenosis, mucosal injury, small-intestinal mucosal injury, undifferentiated spondyloarthritis, sepsis, cerebral ischemic infarction, cerebral infarction, brain trauma, brain injury caused by brain surgery, spinal cord injury, arteriosclerosis, acute respiratory distress syndrome, lung injury caused by hemorrhagic shock, multiple organ failure, neuropathic pain, cerebral vasospasm after subarachnoid hemorrhage, burn, polytrauma, idiopathic interstitial pulmonary fibrosis, epilepsy, status epilepticus, viral encephalitis, influenza encephalopathy, inflammatory bowel disease, Kawasaki disease, multiple sclerosis, bronchial asthma, chronic bronchitis, pulmonary emphysema, organ injury after surgery, organ injury after radiotherapy, nephrotic syndrome, acute kidney injury, acute/chronic rejection after organ transplantation, SLE, rheumatoid arthritis, Behcet's disease, myocarditis, endocarditis, ischemia-reperfusion injury, myocardial infarction, congestive heart failure, adipose tissue inflammation, neutrophilic dermatosis, Sweet's disease, and Stevens-Johnson syndrome.

15. An antibody or an antibody fragment thereof, which is contained as an active ingredient in the pharmaceutical composition of any one of the above-mentioned items 1 to 14.

(A) An antibody or an antibody fragment thereof, which is generated using a heterodimer of S100A8 and S100A9 as an antigen.

(B) The antibody or the antibody fragment thereof according to the above-mentioned item (A), wherein the antibody or the antibody fragment thereof has a neutralizing ability against any one selected from the following items (i) to (iii):
(i) the heterodimer of S100A8 and S100A9;
(ii) the heterodimer of S100A8 and S100A9, and an S100A8 monomer; and
(iii) the heterodimer of S100A8 and S100A9, and an S100A9 monomer.

(C) The antibody or the antibody fragment thereof according to the above-mentioned item (A) or (B), wherein the antibody generated using the heterodimer of S100A8 and S100A9 as the antigen is a monoclonal antibody.

(D) The antibody or the antibody fragment thereof according to the above-mentioned item (C), wherein a subclass of the monoclonal antibody is any one selected from $IgG_1$, $IgG_2$, $IgG_3$, and $IgG_4$.

(E) The antibody or the antibody fragment thereof according to any one of the above-mentioned items (A) to (D),
wherein the antibody or the antibody fragment thereof contains: heavy chain variable regions including a heavy chain variable region 1 (CDR H1), a heavy chain variable region 2 (CDR H2), and a heavy chain variable region 3 (CDR H3); and light chain variable regions including a light chain variable region 1 (CDR L1), a light chain variable region 2 (CDR L2), and a light chain variable region 3 (CDR L3), wherein the heavy chain variable region 1 (CDR H1) contains any one of the amino acid sequences set forth in SEQ ID NO: 7, SEQ ID NO: 10, SEQ ID NO: 13, SEQ ID NO: 16, or SEQ ID NO: 19, or the amino acid sequence having one or a plurality of amino acids deleted, added, substituted, or inserted in SEQ ID NO: 7, 10, 13, 16, or 19, wherein the heavy chain variable region 2 (CDR H2) contains any one of the amino acid sequences set forth in SEQ ID NO: 8, SEQ ID NO: 11, SEQ ID NO: 14, SEQ ID NO: 17, or SEQ ID NO: 20, or the amino acid sequence having one or a plurality of amino acids deleted, added, substituted, or inserted in SEQ ID NO: 8, 11, 14, 17, or 20, wherein the heavy chain variable region 3 (CDR H3) contains any one of the amino acid sequences set forth in SEQ ID NO: 9, SEQ ID NO: 12, SEQ ID NO: 15, SEQ ID NO: 18, or SEQ ID NO: 21, or the amino acid sequence having one or a plurality of amino acids deleted, added, substituted, or inserted in SEQ ID NO: 9, 12, 15, 18, or 21, wherein the light chain variable region 1 (CDR L1) contains any one of the amino acid sequences set forth in SEQ ID NO: 22, SEQ ID NO: 25, SEQ ID NO: 28, SEQ ID NO: 31, or SEQ ID NO: 34, or the amino acid sequence having one or a plurality of amino acids deleted, added, substituted, or inserted in SEQ ID NO: 22, 25, 28, 31, or 34, wherein the light chain variable region 2 (CDR L2) contains any one of the amino acid sequences set forth in SEQ ID NO: 23, SEQ ID NO: 26, SEQ ID NO: 29, SEQ ID NO: 32, or SEQ ID NO: 35, or the amino acid sequence having one or a plurality of amino acids deleted, added, substituted, or inserted in SEQ ID NO: 23, 26, 29, 32, or 35, and wherein the light chain variable region 3 (CDR L3) contains any one of the amino acid sequences set forth in SEQ ID NO: 24, SEQ ID NO: 27, SEQ ID NO: 30, SEQ ID NO: 33, or SEQ ID NO: 36, or the amino acid sequence having one or a plurality of amino acids deleted, added, substituted, or inserted in SEQ ID NO: 24, 27, 30, 33, or 36.

(F) The antibody or the antibody fragment thereof according to the above-mentioned item (E), wherein the heavy chain variable region 1 (CDR H1) contains any one of the amino acid sequences set forth in SEQ ID NO: 7, or the amino acid sequence having one or a plurality of amino acids deleted, added, substituted, or inserted in the amino acid sequence set forth in SEQ ID NO: 7, wherein the heavy chain variable region 2 (CDR H2) contains any one of the amino acid sequences set forth in SEQ ID NO: 8, or the amino acid sequence having one or a plurality of amino acids deleted, added, substituted, or inserted in the amino acid sequence set forth in SEQ ID NO: 8, wherein the heavy chain variable region 3 (CDR H3) contains any one of the amino acid sequences set forth in SEQ ID NO: 9, or the amino acid sequence having one or a plurality of amino acids deleted, added, substituted, or inserted in the amino acid sequence set forth in SEQ ID NO: 9, wherein the light chain variable region 1 (CDR L1) contains any one of the amino acid sequences set forth in SEQ ID NO: 22, or the amino acid sequence having one or a plurality of amino acids deleted, added, substituted, or inserted in the amino acid sequence set forth in SEQ ID NO: 22, wherein the light chain variable region 2 (CDR L2) contains any one of the amino acid sequences set forth in SEQ ID NO: 23, or the amino acid sequence having one or a plurality of amino acids deleted, added, substituted, or inserted in the amino acid sequence set forth in SEQ ID NO: 23, and wherein the light chain variable region 3 (CDR L3) contains any one of the amino acid sequences set forth in SEQ ID NO: 24, or the amino acid sequence having one or a plurality of amino acids deleted, added, substituted, or inserted in the amino acid sequence set forth in SEQ ID NO: 24.

(G) The antibody or the antibody fragment thereof according to the above-mentioned item (E), wherein the heavy chain variable region 1 (CDR H1) contains any one of the amino acid sequences set forth in SEQ ID NO: 10, or the amino acid sequence having one or a plurality of amino acids deleted, added, substituted, or inserted in the amino acid sequence set forth in SEQ ID NO: 10, wherein the heavy chain variable region 2 (CDR H2) contains any one of the amino acid sequences set forth in SEQ ID NO: 11, or the amino acid sequence having one or a plurality of amino acids deleted, added, substituted, or inserted in the amino acid sequence set forth in SEQ ID NO: 11, wherein the heavy chain variable region 3 (CDR H3) contains any one of the amino acid sequences set forth in SEQ ID NO: 12, or the amino acid sequence having one or a plurality of amino acids deleted, added, substituted, or inserted in the amino acid sequence set forth in SEQ ID NO: 12, wherein the light chain variable region 1 (CDR L1) contains any one of the amino acid sequences set forth in SEQ ID NO: 25, or the amino acid sequence having one or a plurality of amino acids deleted, added, substituted, or inserted in the amino acid sequence set forth in SEQ ID NO: 25, wherein the light chain variable region 2 (CDR L2) contains any one of the amino acid sequences set forth in SEQ ID NO: 26, or the amino acid sequence having one or a plurality of amino acids deleted, added, substituted, or inserted in the amino acid sequence set forth in SEQ ID NO: 26, and wherein the light chain variable region 3 (CDR L3) contains any one of the amino acid sequences set forth in SEQ ID NO: 27, or the amino acid sequence having one or a plurality of amino acids deleted, added, substituted, or inserted in the amino acid sequence set forth in SEQ ID NO: 27.

(H) The antibody or the antibody fragment thereof according to the above-mentioned item (E), wherein the heavy chain variable region 1 (CDR H1) contains any one of the amino acid sequences set forth in SEQ ID NO: 13, or the amino acid sequence having one or a plurality of amino acids deleted, added, substituted, or inserted in the amino acid sequence set forth in SEQ ID NO: 13, wherein the heavy chain variable region 2 (CDR H2) contains any one of the amino acid sequences set forth in SEQ ID NO: 14, or the amino acid sequence having one or a plurality of amino acids deleted, added, substituted, or inserted in the amino acid sequence set forth in SEQ ID NO: 14, wherein the heavy chain variable region 3 (CDR H3) contains any one of the amino acid sequences set forth in SEQ ID NO: 15, or the amino acid sequence having one or a plurality of amino acids deleted, added, substituted, or inserted in the amino acid sequence set forth in SEQ ID NO: 15, wherein the light chain variable region 1 (CDR L1) contains any one of the amino acid sequences set forth in SEQ ID NO: 28, or the amino acid sequence having one or a plurality of amino acids deleted, added, substituted, or inserted in the amino acid sequence set forth in SEQ ID NO: 28, wherein the light chain variable region 2 (CDR L2) contains any one of the amino acid sequences set forth in SEQ ID NO: 29, or the amino acid sequence having one or a plurality of amino acids deleted, added, substituted, or inserted in the amino acid sequence set forth in SEQ ID NO: 29, and wherein the light chain variable region 3 (CDR L3) contains any one of the amino acid sequences set forth in SEQ ID NO: 30, or the amino acid sequence having one or a plurality of amino acids deleted, added, substituted, or inserted in the amino acid sequence set forth in SEQ ID NO: 30.

(I) The antibody or the antibody fragment thereof according to the above-mentioned item (E), wherein the heavy chain variable region 1 (CDR H1) contains any one of the amino acid sequences set forth in SEQ ID NO: 16, or the amino acid sequence having one or a plurality of amino acids deleted, added, substituted, or inserted in the amino acid sequence set forth in SEQ ID NO: 16, wherein the heavy chain variable region 2 (CDR H2) contains any one of the amino acid sequences set forth in SEQ ID NO: 17, or the amino acid sequence having one or a plurality of amino acids deleted, added, substituted, or inserted in the amino acid sequence set forth in SEQ ID NO: 17, wherein the heavy chain variable region 3 (CDR H3) contains any one of the amino acid sequences set forth in SEQ ID NO: 18, or the amino acid sequence having one or a plurality of amino acids deleted, added, substituted, or inserted in the amino acid sequence set forth in SEQ ID NO: 18, wherein the light chain variable region 1 (CDR L1) contains any one of the amino acid sequences set forth in SEQ ID NO: 31, or the amino acid sequence having one or a plurality of amino acids deleted, added, substituted, or inserted in the amino acid sequence set forth in SEQ ID NO: 31, wherein the light chain variable region 2 (CDR L2) contains any one of the amino acid sequences set forth in SEQ ID NO: 32, or the amino acid sequence having one or a plurality of amino acids deleted, added, substituted, or inserted in the amino acid sequence set forth in SEQ ID NO: 32, and wherein the light chain variable region 3 (CDR L3) contains any one of the amino acid sequences set forth in SEQ ID NO: 33, or the amino acid sequence having one or a plurality of amino acids deleted, added, substituted, or inserted in the amino acid sequence set forth in SEQ ID NO: 33.

(J) The antibody or the antibody fragment thereof according to the above-mentioned item (E), wherein the heavy chain variable region 1 (CDR H1) contains any one of the amino acid sequences set forth in SEQ ID NO: 19, or the amino acid sequence having one or a plurality of amino acids deleted, added, substituted, or inserted in the amino acid sequence set forth in SEQ ID NO: 19, wherein the heavy chain variable region 2 (CDR H2) contains any one of the amino acid sequences set forth in SEQ ID NO: 20, or the amino acid sequence having one or a plurality of amino acids deleted, added, substituted, or inserted in the amino acid sequence set forth in SEQ ID NO: 20, wherein the heavy chain variable region 3 (CDR H3) contains any one of the amino acid sequences set forth in SEQ ID NO: 21, or the amino acid sequence having one or a plurality of amino acids deleted, added, substituted, or inserted in the amino acid sequence set forth in SEQ ID NO: 21, wherein the light chain variable region 1 (CDR L1) contains any one of the amino acid sequences set forth in SEQ ID NO: 34, or the amino acid sequence having one or a plurality of amino acids deleted, added, substituted, or inserted in the amino acid sequence set forth in SEQ ID NO: 34, wherein the light chain variable region 2 (CDR L2) contains any one of the amino acid sequences set forth in SEQ ID NO: 35, or the amino acid sequence having one or a plurality of amino acids deleted, added, substituted, or inserted in the amino acid sequence set forth in SEQ ID NO: 35, and wherein the light chain variable region 3 (CDR L3) contains any one of the amino acid sequences set forth in SEQ ID NO: 36, or the amino acid sequence having one or a plurality of amino acids deleted, added, substituted, or inserted in the amino acid sequence set forth in SEQ ID NO: 36.

(K) A method of suppressing cancer metastasis and/or a method of treating cancer, including using the pharmaceutical composition of any one of the above-mentioned items 1 to 10.

(L) The method of suppressing cancer metastasis and/or the method of treating cancer according to the above-mentioned item (K), wherein the cancer is one kind or a plurality of kinds of cancers selected from skin cancer, lung cancer, stomach cancer, colon cancer, pancreatic cancer, liver cancer, lung cancer, kidney cancer, breast cancer, uterine cancer, bile duct cancer, esophageal cancer, pharyngeal cancer, biliary tract cancer, bladder cancer, blood cancer, lymphoma, ovarian cancer, prostate cancer, brain tumor, and thyroid cancer.

(M) A method of treating an inflammatory disease, including using the pharmaceutical composition of any one of the above-mentioned items 1 to 10.

(N) The method of treating an inflammatory disease according to the above-mentioned item (M), wherein the inflammatory disease is one kind or a plurality of kinds of inflammatory diseases selected from pulmonary fibrosis, lung injury (including acute lung injury and chronic lung injury), systemic inflammatory response syndrome, chronic obstructive pulmonary disease, elderly-onset rheumatoid arthritis, juvenile rheumatoid arthritis, juvenile idiopathic arthritis, inflammatory arthritis, reactive arthritis, uveitis-associated arthritis, inflammatory bowel disease-associated arthritis, inflammatory bowel disease, skin stress, insulitis, nephritis (including glomerulonephritis and pyelonephritis), cystic fibrosis, periodontitis, cervicitis, peritonitis, cancerous peritonitis, diabetic angiopathy, infectious disease, cardiovascular disease, autoimmune disease, autoinflammatory disease, pneumonia (including interstitial pneumonia and cryptogenic organizing pneumonia), pulmonary tuberculosis, pulmonary nontuberculous mycobacteriosis, pneumomycosis, pyothorax, endometritis, metritis, adnexitis, tuboovarian abscess, pelvic peritonitis, ankylosing spondylitis, psoriasis, psoriatic arthritis, esophagitis, gastroesophageal reflux disease, esophageal ulcer, gastric ulcer, duodenal ulcer, stress ulcer, steroid ulcer, acute gastritis, chronic gastritis, infectious enteritis, acute colitis, appendicitis, chronic enteritis, irritable bowel syndrome, ulcerative colitis, Crohn's disease, nonalcoholic steatohepatitis (NASH), ischemic colitis, acute pancreatitis, chronic pancreatitis, acute cholecystitis, chronic cholecystitis, cholangitis, hepatitis, collagenosis, mucosal injury, small-intestinal mucosal injury, undifferentiated spondyloarthritis, sepsis, cerebral ischemic infarction, cerebral infarction, brain trauma, brain injury caused by brain surgery, spinal cord injury, arteriosclerosis, acute respiratory distress syndrome, lung injury caused by hemorrhagic shock, multiple organ failure, neuropathic pain, cerebral vasospasm after subarachnoid hemorrhage, burn, polytrauma, idiopathic interstitial pulmonary fibrosis, epilepsy, status epilepticus, viral encephalitis, influenza encephalopathy, inflammatory bowel disease, Kawasaki disease, multiple sclerosis, bronchial asthma, chronic bronchitis, pulmonary emphysema, organ injury after surgery, organ injury after radiotherapy, nephrotic syndrome, acute kidney injury, acute/chronic rejection after organ transplantation, SLE, rheumatoid arthritis, Behcet's disease, myocarditis, endocarditis, ischemia-reperfusion injury, myocardial infarction, congestive heart failure, adipose tissue inflammation, neutrophilic dermatosis, Sweet's disease, and Stevens-Johnson syndrome.

Advantageous Effects of Invention

The antibody or the antibody fragment thereof being contained in the pharmaceutical composition of the present invention and having antigen-binding activity for the S100A8/A9 heterodimer suppresses the expression of inflammatory cytokines to be induced by S100A8/A9 and suppresses the migration of S100A8/A9-induced cancer cells in an in vitro system, and further, shows a metastasis-suppressing action on various tumor cells in vivo as well. Further, the antibody or the antibody fragment thereof also effectively acts on inflammatory diseases.

BRIEF DESCRIPTION OF DRAWINGS

FIG. 7 is a diagram for illustrating the outline of measurement of chemotaxis, for the evaluation of the chemotaxis of S100A8/A9-induced cancer cells (Example 3).

FIG. 19 includes photographs showing results about metastasis into lungs in a test according to the protocol illustrated in FIG. 18 (Example 10).

FIG. 20 shows results of the test according to the protocol illustrated in FIG. 18. The figure includes a graph showing the number of foci each having a diameter of 1 mm or more formed in the lungs and photographs (Example 10).

DESCRIPTION OF EMBODIMENTS

Figure 1:
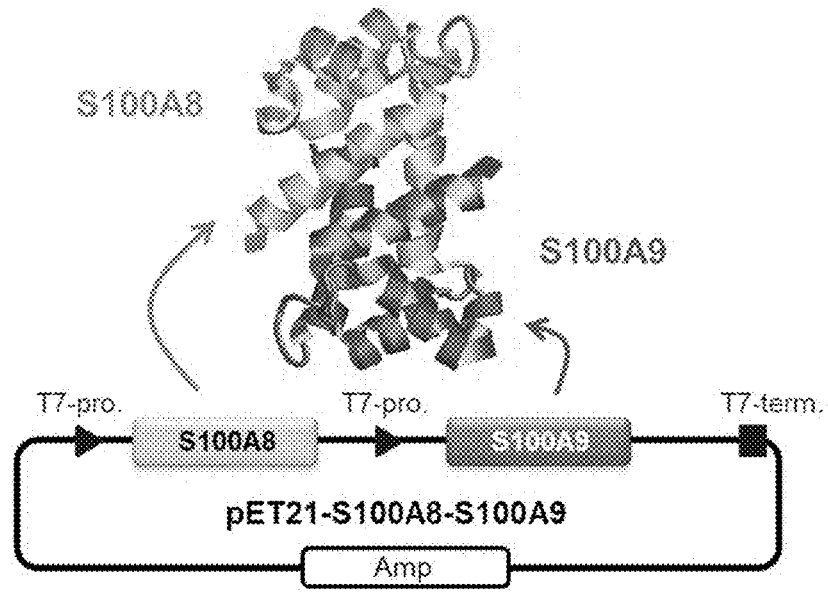
FIG. 1 is a diagram for illustrating the structure of an expression vector for preparing an S100A8/A9 heterodimer serving as an antigen for generating an anti-S100A8/A9 antibody of the present invention (Reference Example 1).

The present invention relates to an antibody or an antibody fragment thereof having antigen-binding activity for an S100A8/A9 heterodimer. The present invention also relates to a pharmaceutical composition containing the anti-S100A8/A9 antibody or the antibody fragment thereof as an active ingredient. The antibody having antigen-binding activity for an S100A8/A9 heterodimer is hereinafter referred to as "anti-S100A8/A9 antibody".

The present invention relates to an anti-S100A8/A9 antibody or an antibody fragment thereof capable of effectively suppressing cancer metastasis, or effective against an inflammatory disease. The anti-S100A8/A9 antibody or the antibody fragment thereof of the present invention is based on an antibody generated using the S100A8/A9 heterodimer as an antigen, and has antigen-binding activity for the S100A8/A9 heterodimer. More specifically, the anti-S100A8/A9 antibody or the antibody fragment thereof of the present invention is an antibody or an antibody fragment thereof that undergoes an antigen-antibody reaction with the S100A8/A9 heterodimer, or with the S100A8/A9 heterodimer and an S100A8 monomer or an S100A9 monomer.

Herein, the term "antibody" is used in its broadest sense, and encompasses monoclonal antibodies, polyclonal antibodies, chimeric antibodies, and multispecific antibodies as long as those antibodies each show antigen-binding activity for the S100A8/A9 heterodimer. Further, the present invention encompasses various antibody structures including antibody fragments thereof. An example of the antibody fragments is an antigen-binding fragment of the antibody.

The anti-S100A8/A9 antibody or the antibody fragment thereof of the present invention may contain a heavy chain variable region (VH-CDR) and/or a light chain variable region (VL-CDR), or a fragment thereof. The class of the antibody refers to the type of constant domain or constant region included in a heavy chain (H chain) of the antibody, and examples thereof include IgA, IgD, IgE, IgG, and IgM. Herein, the class of the antibody is not particularly limited, but is most suitably IgG. As subclasses of IgG, there are given, for example, $IgG_1$, $IgG_2$, $IgG_3$, and $IgG_4$, among which $IgG_1$ or $IgG_2$ is suitable. Examples of the antibody fragment may include Fv, Fab, Fab', Fab'-SH, $F(ab')_2$, and combinations thereof.

The anti-S100A8/A9 antibody or the antibody fragment thereof of the present invention may be a human antibody or a humanized antibody. The human antibody refers to: an antibody produced by a human or human cells; or an antibody including an amino acid sequence corresponding to the amino acid sequence of an antibody derived from a nonhuman supply source using a human antibody repertoire or other human antibody-coding sequences. The humanized antibody may be a chimeric antibody.

The amino acid sequences of VH-CDR and/or VL-CDR contained in the anti-S100A8/A9 antibody or the antibody fragment thereof of the present invention may contain, for example, amino acid sequences identified by the following SEQ ID NOs. For example, a heavy chain variable region 1 (CDR H1) may contain any one amino acid sequence set forth in SEQ ID NO: 7, SEQ ID NO: 10, SEQ ID NO: 13, SEQ ID NO: 16, or SEQ ID NO: 19. A heavy chain variable region 2 (CDR H2) may contain any one amino acid sequence set forth in SEQ ID NO: 8, SEQ ID NO: 11, SEQ ID NO: 14, SEQ ID NO: 17, or SEQ ID NO: 20. A heavy chain variable region 3 (CDR H3) may contain any one amino acid sequence set forth in SEQ ID NO: 9, SEQ ID NO: 12, SEQ ID NO: 15, SEQ ID NO: 18, or SEQ ID NO: 21. For example, a light chain variable region 1 (CDR L1) may contain any one amino acid sequence set forth in SEQ ID NO: 22, SEQ ID NO: 25, SEQ ID NO: 28, SEQ ID NO: 31, or SEQ ID NO: 34. A light chain variable region 2 (CDR L2) region may contain any one amino acid sequence set forth in SEQ ID NO: 23, SEQ ID NO: 26, SEQ ID NO: 29, SEQ ID NO: 32, or SEQ ID NO: 35. A light chain variable region 3 (CDR L3) may contain any one amino acid sequence set forth in SEQ ID NO: 24, SEQ ID NO: 27, SEQ ID NO: 30, SEQ ID NO: 33, or SEQ ID NO: 36. In the present invention, amino acid sequence information on each of the above-mentioned regions is also encompassed in the scope of rights. In addition to the above-mentioned amino acid sequences, even when one or a plurality of amino acids are substituted, deleted, added, or inserted in each of the sequences, anti-S100A8/A9 antibodies or antibody fragments thereof containing such amino acid sequences are also encompassed in the scope of rights of the present invention as long as those antibodies or antibody fragments each show antigen-binding activity for the S100A8/A9 heterodimer.

The anti-S100A8/A9 antibody of the present invention may be generated by a method known per se or any method to be developed in the future, through use of the above-mentioned S100A8/A9 heterodimer as an antigen. For example, the anti-S100A8/A9 antibody may be generated by immunizing a mammal, such as a mouse or a rat, with an antigen. The animal may be immunized using, as an immunogen, a mixture of the S100A8/A9 heterodimer antigen and an adjuvant. The adjuvant is not particularly limited, but examples thereof include Freund's complete adjuvant and Freund's incomplete adjuvant. A method of administering the immunogen at the time of the immunization may be any of the methods known per se, such as subcutaneous injection, intraperitoneal injection, intravenous injection, and intramuscular injection. Of those, subcutaneous injection or intraperitoneal injection is preferred. The immunization may be performed once or a plurality of times at an appropriate interval, preferably a plurality of times at an interval of from 1 week to 5 weeks.

Through use of the S100A8/A9 heterodimer antigen, a monoclonal antibody may also be generated in accordance with a conventional method. Hybridomas that produce the anti-S100A8/A9 antibody may be obtained by immunizing a mammal, such as a mouse or a rat, with the S100A8/A9 heterodimer antigen, collecting lymphocytes from the animal, and fusing myeloma cells thereto in accordance with a conventional method to generate hybridomas. Cells that produce the monoclonal antibody of interest may be obtained by investigating a binding property to the S100A8/A9 heterodimer by an ELISA method or the like for a culture supernatant or the like of the generated hybridomas, and repeating operation of cloning antibody-producing hybridomas. A method known per se or the like may be applied as a method of generating a humanized antibody.

From the antibody-producing hybridoma cells, purification of total RNA and subsequent synthesis of cDNA may be performed in accordance with conventional methods. Through amplification of antibody genes for a full-length heavy chain (H chain) and light chain (L chain) from the resultant cDNA by PCR using respective primers, respective gene fragments may be obtained. Through ligation of the resultant gene fragments to an expression vector, the antibody genes may be cloned. With regard to the amino acid sequences of the H chain and L chain of the antibody, the base sequence of a plasmid vector encoding the amino acid sequences may be identified to determine the amino acid sequence of the antibody. On the basis of the obtained information on the amino acid sequence and the base sequence, the antibody may be generated by a gene recombination technique, or the antibody may be generated by a synthesis method. When the antibody is generated by a gene recombination technique, the antibody may be generated by, for example, a method described in WO 2017/061354 A1.

When the antibody is generated by a gene recombination technique, for example, information on genes encoding respective amino acids that identify CDR H1, CDR H2, CDR H3, CDR L1, CDR L2, and CDR L3 may be utilized. As a specific amino acid sequence, for example, for CDR H1, there is given any one amino acid sequence set forth in SEQ ID NO: 7, SEQ ID NO: 10, SEQ ID NO: 13, SEQ ID NO: 16, or SEQ ID NO: 19. For CDR H2, there is given any one amino acid sequence set forth in SEQ ID NO: 8, SEQ ID NO: 11, SEQ ID NO: 14, SEQ ID NO: 17, or SEQ ID NO: 20. For CDR H3, there is given any one amino acid sequence set forth in SEQ ID NO: 9, SEQ ID NO: 12, SEQ ID NO: 15, SEQ ID NO: 18, or SEQ ID NO: 21. For example, for CDR L1, there is given any one amino acid sequence set forth in SEQ ID NO: 22, SEQ ID NO: 25, SEQ ID NO: 28, SEQ ID NO: 31, or SEQ ID NO: 34. For CDR L2, there is given any one amino acid sequence set forth in SEQ ID NO: 23, SEQ ID NO: 26, SEQ ID NO: 29, SEQ ID NO: 32, or SEQ ID NO: 35. For CDR L3, there is given any one amino acid sequence set forth in SEQ ID NO: 24, SEQ ID NO: 27, SEQ ID NO: 30, SEQ ID NO: 33, or SEQ ID NO: 36. The present invention also encompasses base sequence information encoding respective amino acids that identify the above-identified CDR H1, CDR H2, CDR H3, CDR L1, CDR L2, and CDR L3 and base sequence information on strands complementary thereto. In the present invention, in addition to the above-mentioned base sequence information, even when a base sequence has one to a plurality of nucleotides substituted, deleted, added, or inserted, such base acid sequence information is also encompassed in the scope of rights of the present invention as long as the base sequence allows the anti-S100A8/A9 antibody of the present invention to be generated.

A screening method for the anti-S100A8/A9 antibody of the present invention and investigation methods for evaluating the antibody are specifically described in, for example, Reference Example, Examples, and experimental examples to be described later, but for example, the following methods may also be applied.

Among the above-mentioned antibody-producing hybridomas, hybridomas expressing a plurality of kinds of S100A8/A9 neutralizing antibody candidates may be adapted to serum-free culture and prepared in large amounts for an in vitro or in vivo experiment. A culture supernatant of each clone may be recovered and subjected to the purification of the antibody. Methods known per se or any method to be developed in the future may be applied to the purification of the antibody. For example, the antibody may be recovered by performing affinity chromatography. Specifically, affinity purification using Protein A/G is generally employed, and a column suitable for each animal species or antibody subclass may be used. A purity test for the purified antibody may be performed by a method known per se, and may be performed, for example, by CBB staining.

For evaluation of the anti-S100A8/A9 antibody of the present invention, S100A8/A9-binding decoy protein formulations (exEMMPRIN-Fc, exNPTNβ-Fc, exMCAM-Fc, exRAGE-Fc, and exALCAM-Fc) serving as receptors for S100A8/A9 may be appropriately prepared.

The present invention relates to a pharmaceutical composition, particularly an anticancer agent and/or an anti-inflammatory agent, containing the anti-S100A8/A9 antibody or the antibody fragment thereof as an active ingredient.

The "anticancer agent containing the anti-S100A8/A9 antibody or the antibody fragment thereof as an active ingredient" of the present invention is specifically used as a cancer metastasis suppressor and/or a cancer therapeutic agent. Cancer to be targeted by the anticancer agent of the present invention only needs to be, for example, cancer that may metastasize to a site different from primary cancer, and is not particularly limited, but specific examples thereof include one kind or a plurality of kinds of cancers selected from skin cancer (melanoma), lung cancer, stomach cancer, colon cancer, pancreatic cancer, liver cancer, lung cancer, kidney cancer, breast cancer, uterine cancer, bile duct cancer, esophageal cancer, pharyngeal cancer, biliary tract cancer, bladder cancer, blood cancer, lymphoma, ovarian cancer, prostate cancer, brain tumor, and thyroid cancer. Particularly suitable examples thereof include skin cancer (melanoma), lung cancer, and breast cancer. The site to which the cancer metastasizes is also not particularly limited, but examples thereof include lung, liver, brain, and bone. In particular, metastasis to lung is given. For example, among cancers (malignant tumors) formed in the lung, for example, cancer derived from the lung or bronchial cells is referred to as "primary lung cancer", and cancer formed by "leaping flame" to the lung from any other site in the body, such as skin cancer, breast cancer, or colon cancer, is referred to as "metastatic lung cancer". The primary cancer and the metastatic cancer differ from each other in terms of therapeutic strategies, therapeutic methods, and the like.

It is conceivable that lung metastasis of melanoma is strongly induced in response to S100A8/A9 secreted by the lungs. As the group of receptors for S100A8/A9, as described in the "Background Art" section, there are known, for example, EMMPRIN, NPTNα, NPTNβ, MCAM, and ALCAM. Those receptors are expressed on the cancer cell side, and have a function of catching an S100A8/A9 signal, leading to, for example, lung metastasis of melanoma. Profiling of the S100A8/A9 receptor group in human melanoma, lung cancer, and breast cancer was performed, and found high expressions of EMMPRIN and MCAM in human melanoma, a high expression of NPTNβ in lung cancer, and a high expression of MCAM in breast cancer.

For evaluation of the anti-S100A8/A9 antibody or the antibody fragment thereof of the present invention, an animal model of cancer cell metastasis may be generated. For example, for the metastasis model, for example, B16-BL6 (melanoma), A549 (lung cancer), or MDA-MB-231 (breast cancer) may be used as a cancer cell line reported to undergo lung metastasis in mice. For melanoma, the presence or absence of metastasis can be easily judged by its black color, but in the case of cells for which judgment is difficult, it is also suitable to generate, for example, a line stably expressing a reporter element, such as GFP. For example, in a lung metastasis model of B16-BL6 cells, S100A8/A9-binding decoy protein formulations (exEMMPRIN-Fc, exNPTNβ-Fc, exMCAM-Fc, exRAGE-Fc, and exALCAM-Fc) each show an excellent ability to suppress metastasis.

Examples of the inflammatory disease to be targeted by the "anti-inflammatory agent containing the anti-S100A8/A9 antibody or the antibody fragment thereof as an active ingredient" of the present invention include one kind or a plurality of kinds of inflammatory diseases selected from pulmonary fibrosis, lung injury (including acute lung injury and chronic lung injury), systemic inflammatory response syndrome, chronic obstructive pulmonary disease, elderly-onset rheumatoid arthritis, juvenile rheumatoid arthritis, juvenile idiopathic arthritis, inflammatory arthritis, reactive arthritis, uveitis-associated arthritis, inflammatory bowel disease-associated arthritis, inflammatory bowel disease, skin stress, insulitis, nephritis (including glomerulonephritis and pyelonephritis), cystic fibrosis, periodontitis, cervicitis, peritonitis, cancerous peritonitis, diabetic angiopathy, infectious disease, cardiovascular disease, autoimmune disease, autoinflammatory disease, pneumonia (including interstitial pneumonia and cryptogenic organizing pneumonia), pulmonary tuberculosis, pulmonary nontuberculous mycobacteriosis, pneumomycosis, pyothorax, endometritis, metritis, adnexitis, tubo-ovarian abscess, pelvic peritonitis, ankylosing spondylitis, psoriasis, psoriatic arthritis, esophagitis, gastroesophageal reflux disease, esophageal ulcer, gastric ulcer, duodenal ulcer, stress ulcer, steroid ulcer, acute gastritis, chronic gastritis, infectious enteritis, acute colitis, appendicitis, chronic enteritis, irritable bowel syndrome, ulcerative colitis, Crohn's disease, nonalcoholic steatohepatitis (NASH), ischemic colitis, acute pancreatitis, chronic pancreatitis, acute cholecystitis, chronic cholecystitis, cholangitis, hepatitis, collagenosis, mucosal injury, small-intestinal mucosal injury, undifferentiated spondyloarthritis, sepsis, cerebral ischemic infarction, cerebral infarction, brain trauma, brain injury caused by brain surgery, spinal cord injury, arteriosclerosis, acute respiratory distress syndrome, lung injury caused by hemorrhagic shock, multiple organ failure, neuropathic pain, cerebral vasospasm after subarachnoid hemorrhage, burn, polytrauma, idiopathic interstitial pulmonary fibrosis, epilepsy, status epilepticus, viral encephalitis, influenza encephalopathy, inflammatory bowel disease, Kawasaki disease, multiple sclerosis, bronchial asthma, chronic bronchitis, pulmonary emphysema, organ injury after surgery, organ injury after radiotherapy, nephrotic syndrome, acute kidney injury, acute/chronic rejection after organ transplantation, SLE, rheumatoid arthritis, Behcet's disease, myocarditis, endocarditis, ischemia-reperfusion injury, myocardial infarction, congestive heart failure, adipose tissue inflammation, neutrophilic dermatosis, Sweet's disease, and Stevens-Johnson syndrome. Particularly preferred examples thereof include pulmonary fibrosis, acute lung injury, chronic obstructive pulmonary disease, pneumonia (including interstitial pneumonia and cryptogenic organizing pneumonia), pulmonary tuberculosis, pulmonary nontuberculous mycobacteriosis, and pneumomycosis.

The "pharmaceutical composition containing the anti-S100A8/A9 antibody or the antibody fragment thereof as an active ingredient" of the present invention may be locally administered, or may be systemically administered. A formulation of the antibody to be used in accordance with the present invention is optionally prepared in a freeze-dried formulation or water-soluble form for storage by mixing the antibody having a desired purity with a pharmaceutically acceptable carrier, excipient, or stabilizer. Formulations for parenteral administration may include sterilized, aqueous or nonaqueous solutions, suspensions, and emulsions. Examples of nonaqueous diluents are propylene glycol, polyethylene glycol, plant oils, such as olive oil, and organic ester compositions, such as ethyl oleate, which are suitable for injection. Aqueous carriers may include water, alcoholic/aqueous solutions, emulsions, suspensions, saline, and buffered media. Parenteral carriers may include sodium chloride solution, Ringer's dextrose, dextrose, and sodium chloride, lactated Ringer's, and fixed oils. Intravenous carriers may include, for example, fluid replenishers, and nutrient and electrolyte replenishers (such as those based on Ringer's dextrose). A therapeutic drug for a disease caused by neutrophil activation and/or an inflammatory disease accompanied by neutrophil activation of the present invention may further contain a preservative and other additives, such as an antimicrobial compound, an antioxidant, a chelating agent, and an inert gas.

The "pharmaceutical composition containing the anti-S100A8/A9 antibody or the antibody fragment thereof as an active ingredient" of the present invention may contain two or more active compounds as required for a specific indication to be treated. When the pharmaceutical composition is an anticancer agent, an anticancer agent known per se, an anticancer agent to be developed in the future, and for example, any other medicaments, capable of alleviating a side effect that preferably have complementary activities that do not adversely affect each other, may be used in combination. When the pharmaceutical composition is an anti-inflammatory agent, an anti-inflammatory agent known per se, an anti-inflammatory agent to be developed in the future, and for example, any other medicaments, capable of alleviating a side effect that preferably have complementary activities that do not adversely affect each other may be used in combination.

The "pharmaceutical composition containing the anti-S100A8/A9 antibody or the antibody fragment thereof as an active ingredient" of the present invention contains a therapeutically effective amount of the anti-S100A8/A9 antibody or the antibody fragment thereof. The "therapeutically effective amount" refers to an amount effective, at dosages and for periods of time necessary, to achieve a desired therapeutic result. The therapeutically effective amount may vary depending on factors such as the disease state, age, sex, and body weight of an individual, and the ability of the pharmaceutical to elicit a desired response in the individual.

The pharmaceutical composition of the present invention may be used in the following manner: a single dose or divided doses thereof are used generally every 24 hours, 12 hours, 8 hours, 6 hours, 4 hours, or 2 hours or any combination thereof, generally at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 after the start of treatment, or at least once in week 1, 2, 3, 4, 5, 6, 7, 8, 9, 10, 11, 12, 13, 14, 15, 16, 17, 18, 19, or 20, or any combination thereof, at a daily dose in terms of daily antibody amount of from about 0.1 mg/kg body weight to about 100 mg/kg body weight, for example, 0.5 mg/kg body weight, 0.9 mg/kg body weight, 1.0 mg/kg body weight, 1.1 mg/kg body weight, 1.5 mg/kg body weight, 2 mg/kg body weight, 3 mg/kg body weight, 4 mg/kg body weight, 5 mg/kg body weight, 6 mg/kg body weight, 7 mg/kg body weight, 8 mg/kg body weight, 9 mg/kg body weight, 10 mg/kg body weight, 11 mg/kg body weight, 12 mg/kg body weight, 13 mg/kg body weight, 14 mg/kg body weight, 15 mg/kg body weight, 16 mg/kg body weight, 17 mg/kg body weight, 18 mg/kg body weight, 19 mg/kg body weight, 20 mg/kg body weight, 21 mg/kg body weight, 22 mg/kg body weight, 23 mg/kg body weight, 24 mg/kg body weight, 25 mg/kg body weight, 26 mg/kg body weight, 27 mg/kg body weight, 28 mg/kg body weight, 29 mg/kg body weight, 30 mg/kg body weight, 40 mg/kg body weight, 45 mg/kg body weight, 50 mg/kg body weight, 60 mg/kg body weight, 70 mg/kg body weight, 80 mg/kg body weight, 90 mg/kg body weight, or 100 mg/kg body weight.

EXAMPLES

Now, the results of experiments performed to complete the present invention are shown as Reference Example, and the present invention is more specifically described in Examples. However, the present invention is not limited thereto, and various applications are possible without departing from the technical concept of the present invention.

(Reference Example 1) Preparation of S100A8/A9 Heterodimer for Generating Anti-S100A8/A9 Antibodies In this Reference Example, the preparation of an S100A8/A9 heterodimer serving as an antigen for the generation of anti-S100A8/A9 antibodies shown in subsequent Examples is described. The S100A8/A9 heterodimer was generated with *Escherichia coli* using an expression vector obtained by incorporating full-length S100A8 and full-length S100A9 into pET21 (see FIG. 1), and was purified (see Non Patent Literature 8). For comparative examples, full-length S100A8 or full-length S100A9 was incorporated into pET21, generated with *Escherichia coli* by the same technique as above, and purified (see Non Patent Literature 8).

Figure 2:
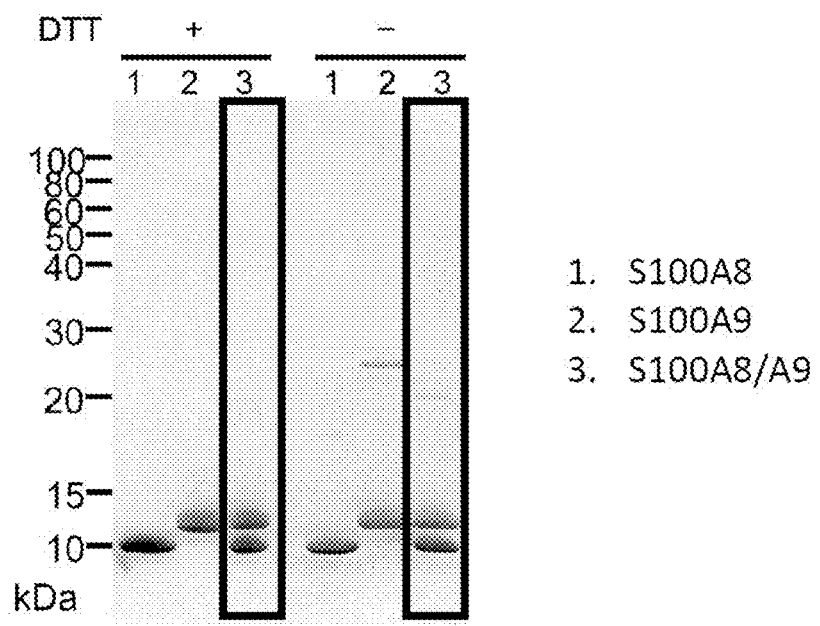
FIG. 2 is a photograph showing results obtained by subjecting a purified S100A8/A9 heterodimer, S100A8 monomer, and S100A9 monomer to SDS-PAGE, followed by CBB staining (Reference Example 1).
Figure 3:
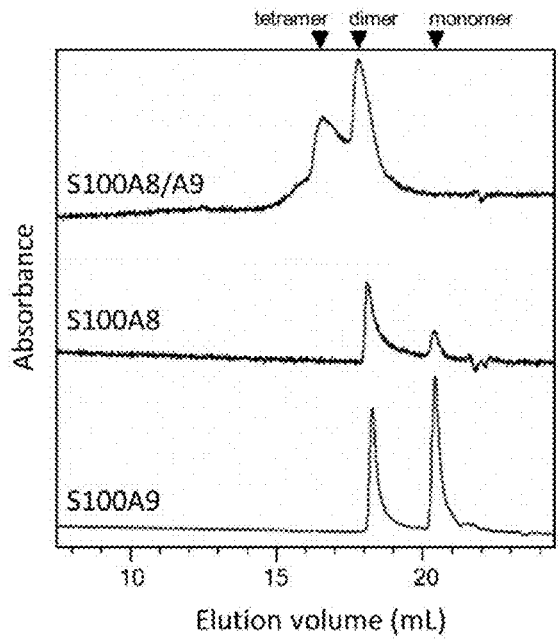
FIG. 3 is a chart showing the results of HPLC analysis of the purified S100A8/A9 heterodimer, S100A8 monomer, and S100A9 monomer (Reference Example 1).

The purified S100A8/A9 heterodimer, and S100A8 monomer and S100A9 monomer serving as comparative examples were subjected to SDS-PAGE, followed by CBB staining. The results are shown in FIG. 2. The S100A8/A9 heterodimer had nearly equal amounts of S100A8 and S100A9, and hence was recognized to have been purified to a high purity. Further, the S100A8/A9 heterodimer was subjected to HPLC analysis. As a result, the results of comparison among the structures of S100A8, S100A9, and S100A8/A9 were as follows: only S100A8/A9 had no monomer presence recognized and mostly had a dimer structure (see FIG. 3). Meanwhile, S100A8 and S100A9 generated as comparative examples were each a mixture of a monomer and a dimer (see FIG. 3).

Figure 4:
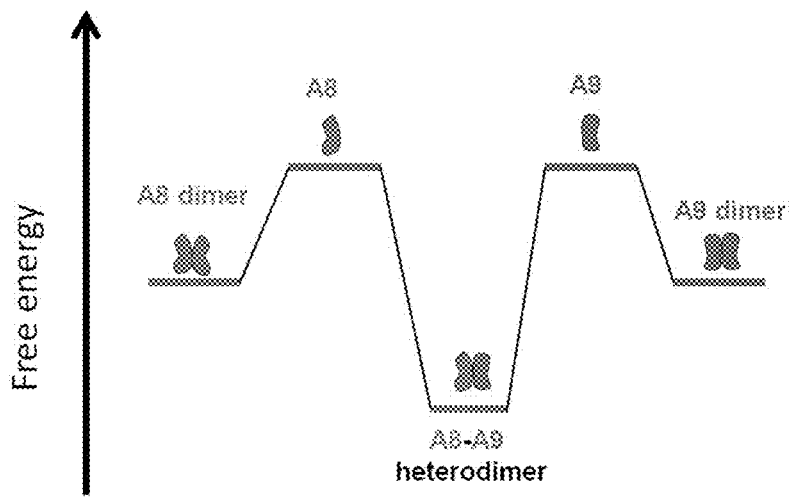
FIG. 4 is a diagram for illustrating the thermodynamic stabilities of the purified S100A8/A9 heterodimer, S100A8 monomer, and S100A9 monomer (Reference Example 1).

In FIG. 4, it is illustrated that a naturally occurring S100A8/A9 heterodimer (abbreviated simply as "A8-A9 heterodimer") is thermodynamically stable, but S100A8 (abbreviated simply as "A8") and S100A9 (abbreviated simply as "A9") each form a homodimer, and hence it is difficult to generate a stable S100A8/A9 heterodimer by mixing S100A8 and S100A9. The S100A8/A9 heterodimer prepared by the method of this Reference Example has high stability, and can be used as an S100A8/A9 heterodimer antigen for generating antibodies in subsequent Examples.

(Example 1) Generation of Anti-S100A8/A9 Monoclonal Antibodies

In this Example, the generation of anti-S100A8/A9 monoclonal antibodies to be used in the following Examples and experimental examples is described. The anti-S100A8/A9 monoclonal antibodies of this Example were generated using S100A8/A9 prepared in the foregoing (Reference Example 1) as an antigen.

(1) Generation of Hybridomas

The anti-S100A8/A9 monoclonal antibodies of this Example were generated through use of S100A8/A9 prepared in the foregoing (Reference Example 1) as an antigen and through utilization of a monoclonal antibody on-contract service, GenoStaff (Nippon Genetics). Mice (Balb/c) were used as immunized animals, and Titer-MAX was used as an adjuvant in immunization with the antigen. In accordance with a conventional method, the spleen of the immunized animals and mouse myeloma cells (P3U1) were fused using polyethylene glycol (PEG1500) to generate hybridomas, affording 160 clones.

(2) Cloning of Hybridomas and Generation of Antibodies

Figure 5:
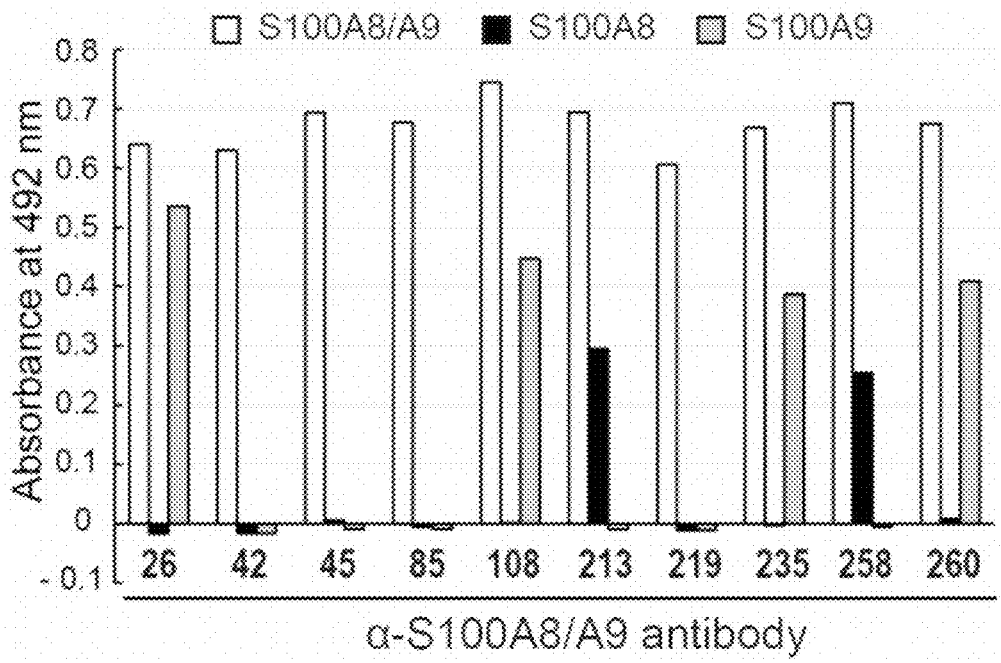
FIG. 5 is a graph showing the results of an investigation, by an ELISA method, of the neutralizing abilities of 10 clones selected from hybridomas for generating anti-S100A8/A9 antibodies against the S100A8/A9 heterodimer, S100A8, or S100A9 (Example 1).

The 160 clones of hybridomas obtained above were subjected to ELISA screening by immobilizing the S100A8/A9 heterodimer, S100A8, or S100A9. Thus, 10 clones shown in FIG. 5 were selected. Hybridomas expressing the selected S100A8/A9 neutralizing antibody ("α-S100A8/A9 antibody" shown in FIG. 5) candidates were adapted to serum-free culture and prepared in large amounts for in vitro and in vivo experiments. A culture supernatant of each clone was recovered and purified with a Protein G column to prepare several milligrams of protein for each of all the clones. A purity test by CBB staining was performed, and as a result, no band other than that of the protein of interest was detected at all. Thus, it was recognized that purified antibodies were prepared at high purities.

(3) Reactivity of Monoclonal Antibodies

The 10 clones selected in (2) above were each investigated for its reactivity against S100A8/A9 heterodimer, S100A8, or S100A9 and subclass, which are shown in Table 1.

TABLE 1

| Clone No. | Reactivity | | | Subclass |
|---|---|---|---|---|
| | S100A8/A9 | S100A8 | S100A9 | |
| 26 | ○ | x | ○ | IgG1 κ |
| 42 | ○ | x | x | IgG2b κ |

TABLE 1-continued

| Clone No. | Reactivity | | | Subclass |
| --- | --- | --- | --- | --- |
| | S100A8/A9 | S100A8 | S100A9 | |
| 45 | ○ | x | x | IgG1 κ |
| 85 | ○ | x | x | IgG2b κ |
| 108 | ○ | x | ○ | IgG1 κ |
| 213 | ○ | ○ | x | IgG2b κ |
| 219 | ○ | x | x | IgG2b κ |
| 235 | ○ | x | ○ | IgG2b κ |
| 258 | ○ | ○ | x | IgG2b κ |
| 260 | ○ | x | ○ | IgG1 κ |

(Example 2) Screening for Neutralizing Antibodies

In this Example, for the monoclonal antibodies produced from the 160 clones of hybridomas generated and selected in Example 1, their influences on the production amounts of S100A8/A9-induced inflammatory cytokines were investigated. Through use of human keratinocytes in which inflammatory cytokines were strongly induced by S100A8/A9, the S100A8/A9 signal-suppressing effect of each antibody was evaluated with the mRNA expression amounts of the inflammatory cytokines serving as indicators. Specifically, 30 ng/mL of purified S100A8/A9 and each anti-S100A8/A9 monoclonal antibody purified with the Protein G column from 1 mL of the culture supernatant of each of the 160 clones of hybridomas were added to keratinocytes (NHK), and after culture at 37° C. for 3 hours, the cells were recovered, followed by real-time quantitative PCR (qPCR) analysis for the respective mRNA expression amounts of TNF-α, IL-6, and IL-8.

The real-time quantitative PCR (qPCR) analysis was performed using a LightCycler rapid thermal cycler system (ABI 7900HT; Applied Biosystems). Measurement was performed using forward (Fwd) and reverse (Rev) primers having the following base sequences.

```
For TNFα measurement
Fwd:
                                (SEQ ID NO: 1)
GACAAGCCTGTAGCCCATGT Rev:
                                (SEQ ID NO: 2)
TCTCAGCTCCACGCCATT For IL-6 measurement
Fwd:
                                (SEQ ID NO: 3)
CTTCCCTGCCCCAGTACC Rev:
                                (SEQ ID NO: 4)
CTGAAGAGGTGAGTGGCTGTC For IL-8 measurement
Fwd:
                                (SEQ ID NO: 5)
AGACAGCAGAGCACACAAGC Rev:
                                (SEQ ID NO: 6)
AGGAAGGCTGCCAAGAGAG
```

Figure 6:
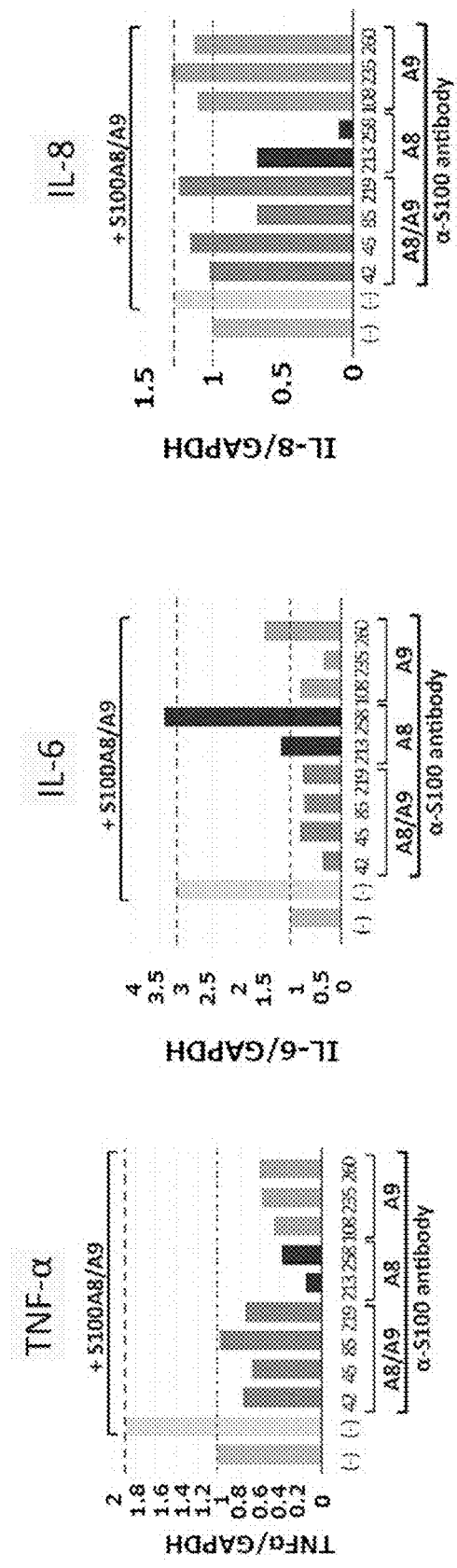
FIG. 6 includes graphs showing the results of an investigation of the expression-suppressing actions of 10 clones selected from hybridomas for generating anti-S100A8/A9 antibodies on each of TNF-α, IL-6, and IL-8 through use of human keratinocytes having inflammatory cytokines strongly induced by S100A8/A9 (Example 2).

As the results of the foregoing, measurement results of the S100A8/A9 (abbreviated simply as "A8/A9")-induced inflammatory cytokines (TNF-α, IL-6, and IL-8) in the presence of the 10 selected clones (Clone Nos.: 26, 42, 45, 85, 108, 213, 219, 235, 258, and 260) are shown in FIG. 6.

On the basis of the results, five kinds of antibodies having particularly high suppressive capacities (one kind of antibody reactive to S100A8 (abbreviated simply as "A8"), two kinds of antibodies reactive to S100A9 (abbreviated simply as "A9"), and two kinds of antibodies reactive only to an S100A8/A9 complex (abbreviated simply as "A8/A9")) were selected. In addition, "α-S100A8/A9 antibody" in FIG. 6 means anti-S100A8/A9 monoclonal antibody.

(Example 3) Evaluation of Chemotaxis of S100A8/A9-induced Cancer Cells

In this Example, for the monoclonal antibodies produced from the 160 clones of hybridomas generated and selected in Example 1, their influences on the chemotaxis of cancer cells induced by S100A8/A9 were investigated using a minute cell chemotaxis measurement apparatus TAXiScan™ (GE Healthcare). Profiling of the S100A8/A9 receptor group in human melanoma, lung cancer, and breast cancer was performed, and found high expressions of EMMPRIN and MCAM in human melanoma, a high expression of NPTNβ, in lung cancer, and a high expression of MCAM in breast cancer. Five kinds of S100A8/A9-binding decoy protein formulations (exEMMPRIN-Fc, exNPTNβ-Fc, exMCAM-Fc, exRAGE-Fc, and exALCAM-Fc) each excellently suppress the migration of S100A8/A9-induced cancer cells. In particular, exEMMPRIN-Fc and exNPTNβ-Fc each show high effects on all of the three kinds of cancer cells. In view of this, for respective cells of B16-BL6 (melanoma), A549 (lung cancer), and MDA-MB-231 (breast cancer), the anti-S100A8/A9 antibody of the present invention was also similarly investigated for its influences on the chemotaxis of cancer cells induced by S100A8/A9.

Respective cancer cells of B16-BL6 (melanoma), A549 (lung cancer), and MDA-MB-231 (breast cancer) were cultured using, for example, a medium containing 10% FBS in D/F medium (Thermo Fisher Scientific). For measurement, the cells were suspended at $2 \times 10^6$ cells/ml in an assay buffer (0.1% mouse serum/RPMI1640/25 mM HEPES). One chamber was loaded with a ligand (S100A8/A9 and monoclonal antibodies generated in Example 1), the other chamber was loaded with cells, and the chemotaxis of each type of cells was measured. The outline of the measurement of the chemotaxis is illustrated in FIG. 7.

Figures 2, 8:
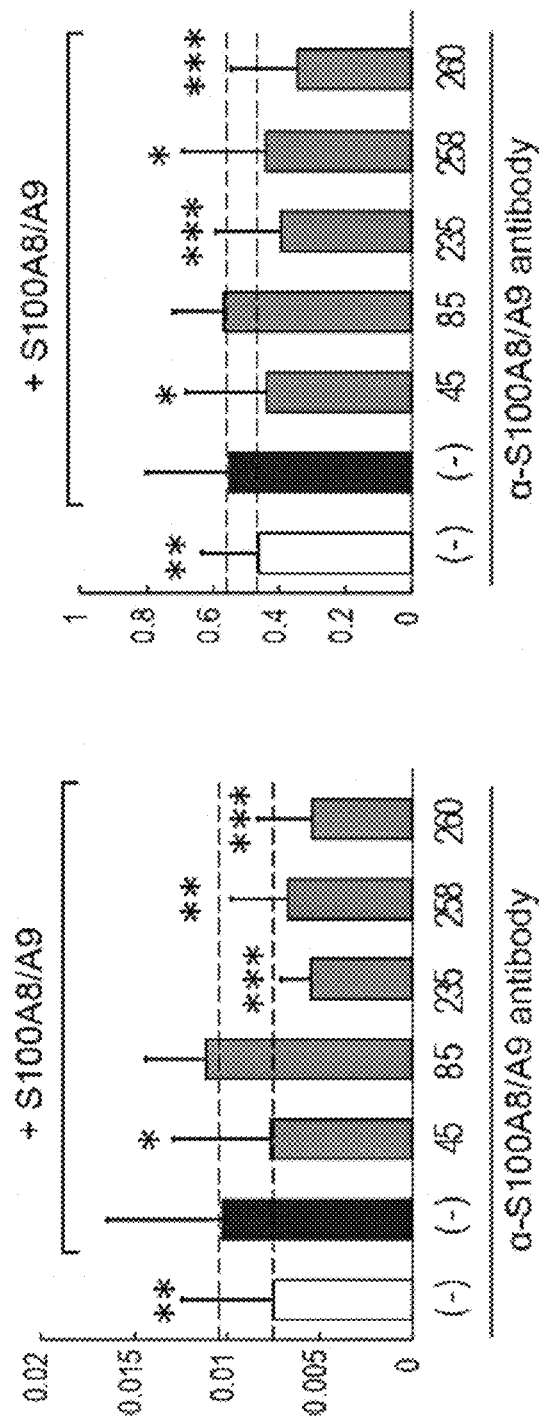
FIG. 8 includes graphs showing the results of an investigation of the migration ability of S100A8/A9-induced cancer cells in terms of velocity and directionality of cell chemotaxis for respective cancer cells of B16-BL6 (melanoma), A549 (lung cancer), and MDA-MB-231 (breast cancer) (Example 3).

The migration ability of each type of cells in the presence of each of the 5 selected clones (Clone Nos.: 45, 85, 235, 258, and 260) was investigated in terms of velocity and directionality of cell chemotaxis (FIG. 8). In FIG. 8, "α-S100A8/A9 antibody" means anti-S100A8/A9 monoclonal antibody. As a result, Clone No. 45 showed a particularly strong migration property-suppressing action.

(Example 4) Lung Metastasis-Suppressing Effect in Tail Vein Injection of Mouse Breast Cancer 4T1 Cells Through use of a lung metastasis model of mouse breast cancer 4T1 cells, the lung metastasis-suppressing effects of anti-S100A8/A9 monoclonal antibodies were investigated.

Figure 10:
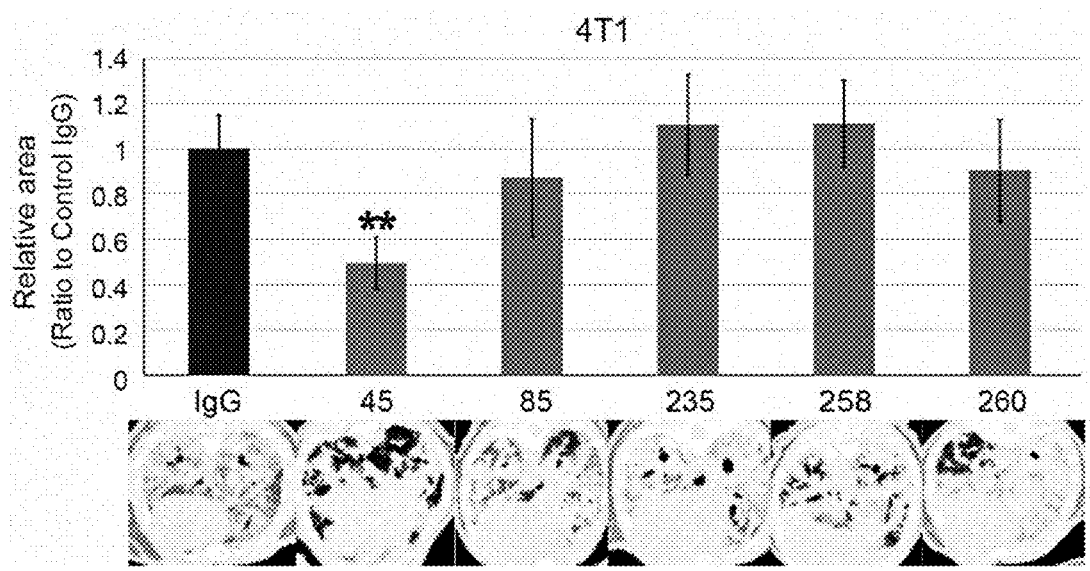
FIG. 10 includes a graph and images showing the results of a test according to the protocol illustrated in FIG. 9, wherein the results are a typical CT image in each CT scan and the area of tumor cells calculated from the CT image compared to those of a negative control group (Example 4).
Figure 9:
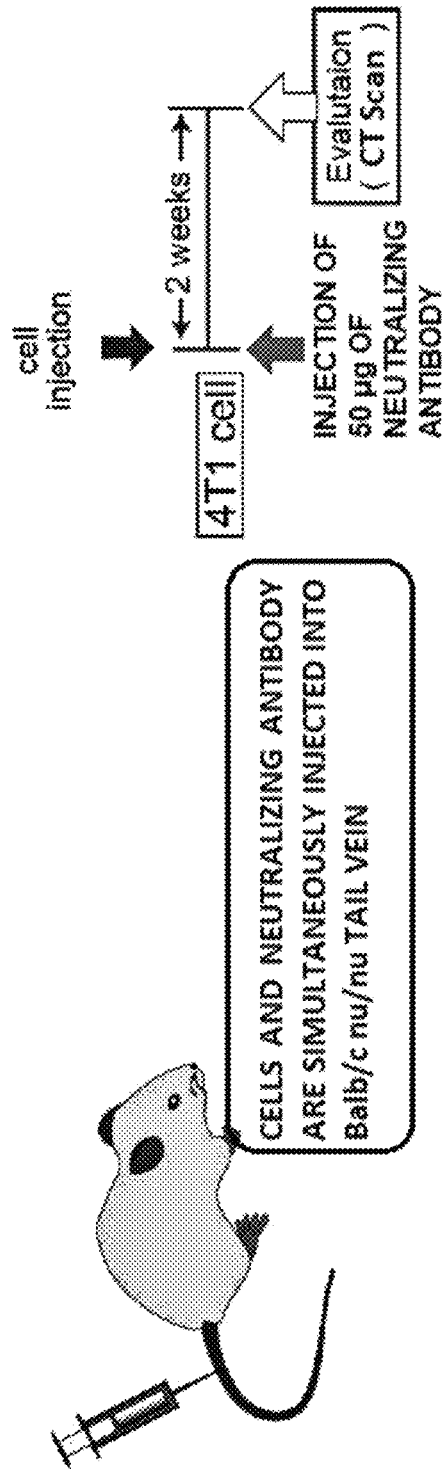
FIG. 9 is a diagram for illustrating a protocol for investigating the lung metastasis-suppressing effect of an anti-S100A8/A9 monoclonal antibody through use of a lung metastasis model of mouse breast cancer 4T1 cells (Example 4).

In accordance with a protocol illustrated in FIG. 9, $1 \times 10^5$ mouse breast cancer 4T1 cells and 50 μg of each anti-S100A8/A9 monoclonal antibody (Clone Nos.: 45, 85, 235, 258, and 260) were simultaneously injected into the tail vein of five Balb/c nu/nu mice per group, and 2 weeks later, CT scans were performed. FIG. 10 shows the results for comparing typical CT images and the areas of tumor cells calculated from the CT images to those of a negative control group. As a result, it was recognized that Clone No. 45 showed a significant lung metastasis-suppressing effect.

(Example 5) Lung Metastasis-Suppressing Effect in Tail Vein Injection of Human Breast Cancer MDA-MB-231 Cells In this Example, the lung metastasis-suppressing effects of anti-S100A8/A9 monoclonal antibodies were investigated. Through use of a lung metastasis model of human breast cancer MDA-MB-231 cells, the lung metastasis-suppressing effects of anti-S100A8/A9 monoclonal antibodies were investigated. For the MDA-MB-231 cells, a line stably expressing GFP was generated.

Figure 11:
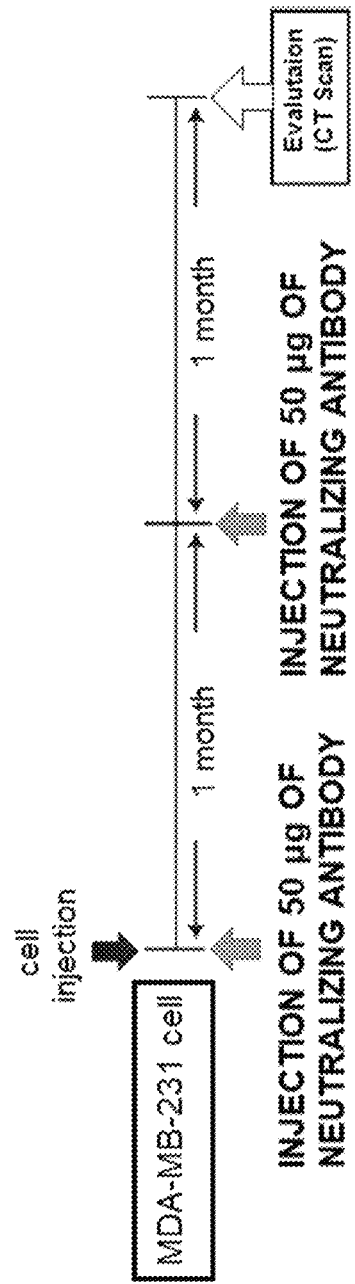
FIG. 11 is a diagram for illustrating a protocol for investigating the lung metastasis-suppressing effect of an anti-S100A8/A9 monoclonal antibody through use of a lung metastasis model of human breast cancer MDA-MB-231 cells (Example 5).
Figure 12:
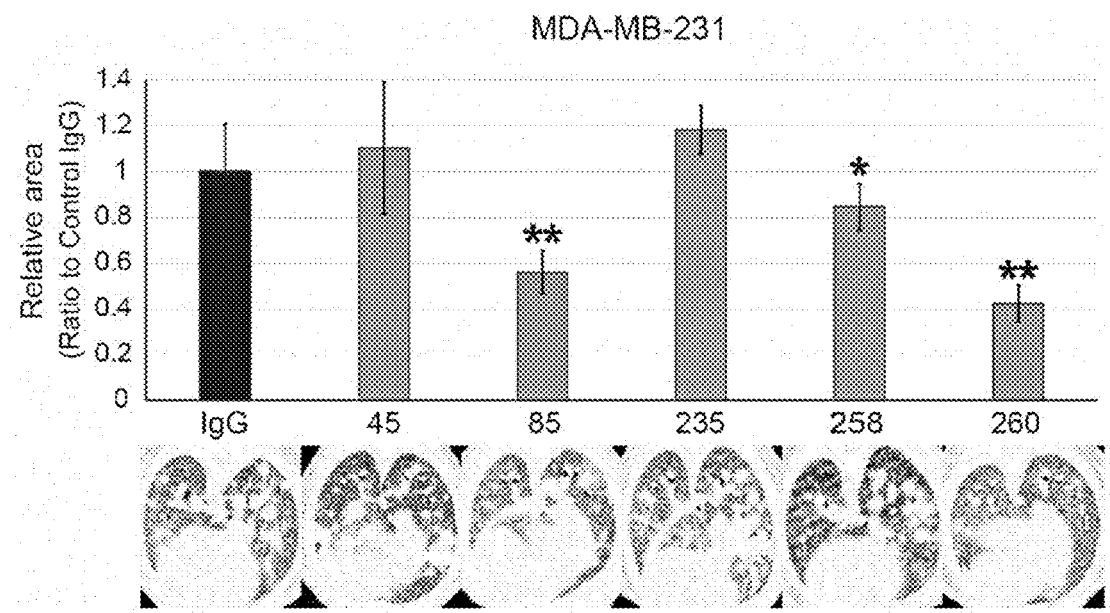
FIG. 12 includes a graph and images showing the results of a test according to the protocol illustrated in FIG. 11, wherein the results are a typical CT image in each CT scan and the area of tumor cells calculated from the CT image compared to those of a negative control group (Example 5).

In accordance with a protocol illustrated in FIG. 11, $1 \times 10^5$ human breast cancer MDA-MB-231 cells and 50 μg of each anti-S100A8/A9 monoclonal antibodies (Clone Nos.: 45, 85, 235, 258, and 260) were simultaneously injected into the tail vein of each five Balb/c nu/nu mice per group, and 1 month later, CT scans were performed. FIG. 12 shows the results for comparing typical CT images and the areas of tumor cells calculated from the CT images to those of a negative control group.

As a result, it was recognized that Clone Nos. 85, 258, and 260 showed significant lung metastasis-suppressing effects. For the MDA-MB-231 cells, mouse lung metastasis was hardly found, suggesting a need for a further investigation on the generation of a metastasis model.

(Example 6) Lung Metastasis-Suppressing Effect in Tail Vein Injection of Mouse Melanoma B16-BL6

Through use of a lung metastasis model of mouse melanoma B16-BL6 cells, the lung metastasis-suppressing effects of anti-S100A8/A9 monoclonal antibodies were investigated. For melanoma, the presence or absence of metastasis can be easily judged by its black color.

Figure 13:
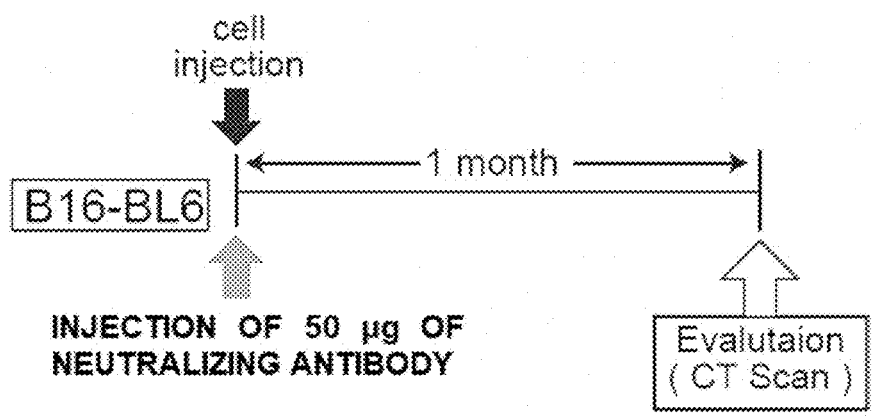
FIG. 13 is a diagram for illustrating a protocol for investigating the lung metastasis-suppressing effect of the anti-S100A8/A9 monoclonal antibody through use of a lung metastasis model of mouse melanoma B16-BL6 cells (Example 6).
Figure 14:
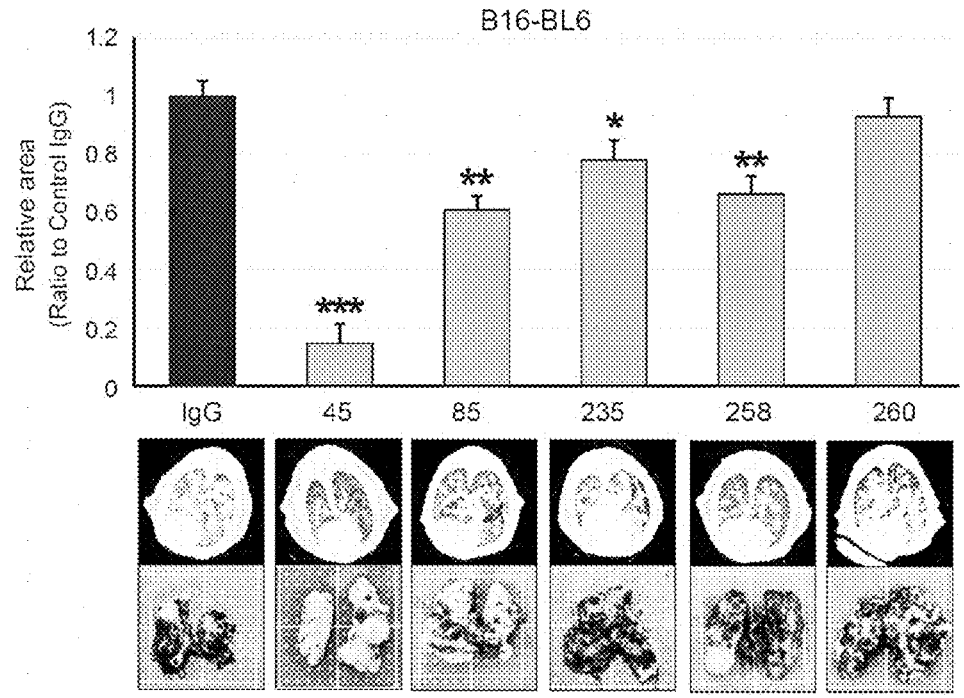
FIG. 14 includes a graph and images showing the results of a test according to the protocol illustrated in FIG. 13, wherein the results are typical lung and CT images in each CT scan and an area calculated from the CT image compared to those of a negative control group (Example 6).

In accordance with a protocol illustrated in FIG. 13, $1 \times 10^5$ mouse melanoma B16-BL6 cells and 50 μg of each anti-S100A8/A9 monoclonal antibodies (Clone Nos.: 45, 85, 235, 258, and 260) were simultaneously injected into the tail vein of five Balb/c nu/nu mice per group, and 1 month later, CT scans were performed. FIG. 14 shows the results for comparing typical mouse lung and CT images and areas calculated from the CT images to those of a negative control group. As a result, it was recognized that Clone Nos. 45, 85, 235, and 258 showed significant lung metastasis-suppressing effects. In particular, Clone No. 45 was found to have a strong metastasis-suppressing effect.

(Example 7) Amino Acid Sequences of Variable Regions of Selected Antibodies

For the five kinds of anti-S100A8/A9 monoclonal antibodies (Clone Nos.: 45, 85, 235, 258, and 260) selected by the screening described above, the sequences of the variable regions of their heavy chains and light chains were analyzed.

```
VH-CDR
Clone No. 45:
CDR H1:
                                    (SEQ ID NO: 7)
SYWMQ Clone No. 45:
CDR H2:
                                    (SEQ ID NO: 8)
AIYPGDGDTRDTQKFKG Clone No. 45:
CDR H3:
                                    (SEQ ID NO: 9)
MAGYNYDNDY Clone No. 85:
CDR H1:
                                    (SEQ ID NO: 10)
SGYNWH Clone No. 85:
CDR H2:
                                    (SEQ ID NO: 11)
YIQYSGSTNYNPSLKS Clone No. 85:
CDR H3:
                                    (SEQ ID NO: 12)
ALRYDYSWFAY Clone No. 235:
CDR H1:
                                    (SEQ ID NO: 13)
NFWMN Clone No. 235:
CDR H2:
                                    (SEQ ID NO: 14)
QIYPGKSDTNYNGKFKG Clone No. 235:
CDR H3:
                                    (SEQ ID NO: 15)
WGAYYKYGGSYFDY Clone No. 258:
CDR H1:
                                    (SEQ ID NO: 16)
TASMGVS Clone No. 258:
CDR H2:
                                    (SEQ ID NO: 17)
HIYWDDDKRYNPSLKS Clone No. 258:
CDR H3:
                                    (SEQ ID NO: 18)
RPLGYFDV Clone No. 260:
CDR H1:
                                    (SEQ ID NO: 19)
NYGVH Clone No. 260:
CDR H2:
                                    (SEQ ID NO: 20)
VVWAGGSTNYNSALMS Clone No. 260:
CDR H3:
                                    (SEQ ID NO: 21)
ARDYYGYDGYFGA VL-CDR
Clone No. 45:
CDR L1:
                                    (SEQ ID NO: 22)
KASQDINKYIA Clone No. 45:
CDR L2:
                                    (SEQ ID NO: 23)
YTSTLQP Clone No. 45:
CDR L3:
                                    (SEQ ID NO: 24)
LQYDNLRT
```

-continued

Clone No. 85:
CDR L1:
(SEQ ID NO: 25)
KASQDVSTAVA

Clone No. 85:
CDR L2:
(SEQ ID NO: 26)
SASYRYT

Clone No. 85:
CDR L3:
(SEQ ID NO: 27)
QQHYSTPLT

Clone No. 235:
CDR L1:
(SEQ ID NO: 28)
SASQGISNYLN

Clone No. 235:
CDR L2:
(SEQ ID NO: 29)
YTSSLHS

Clone No. 235:
CDR L3:
(SEQ ID NO: 30)
QQYSKFPYT

Clone No. 258:
CDR L1:
(SEQ ID NO: 31)
KASQDINNYIS

Clone No. 258:
CDR L2:
(SEQ ID NO: 32)
YTSTLQP

Clone No. 258:
CDR L3:
(SEQ ID NO: 33)
LQYDNLLWT

Clone No. 260:
CDR L1:
(SEQ ID NO: 34)
KASQDINSYLT

Clone No. 260:
CDR L2:
(SEQ ID NO: 35)
RANRLVD

Figure 15:
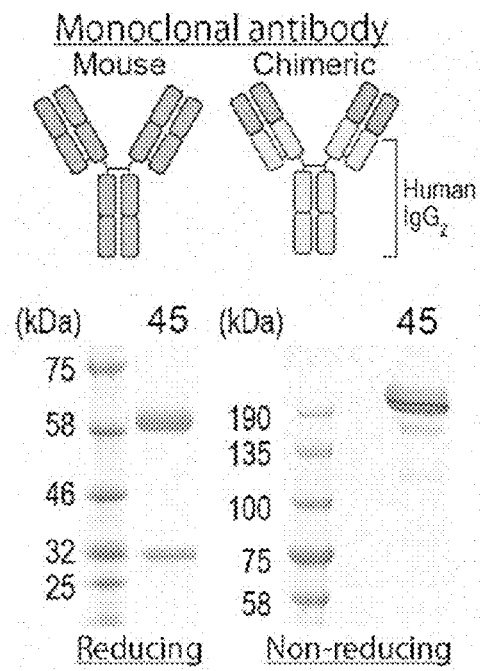
FIG. 15 is a diagram for illustrating the configuration of a chimeric antibody obtained by fusing the Fc portion of human IgG$_2$ to the Fab domain of an S100A8/A9 monoclonal antibody (Clone No. 45) (Example 8).

Clone No. 260:
CDR L3:
(SEQ ID NO: 36)
LQYDEFPLT (Example 8) Generation of Anti-S100A8/A9 Chimeric Antibody In this Example, a chimeric antibody having the Fc portion of human $IgG_2$ fused to the Fab domain of the S100A8/A9 monoclonal antibody (Clone No. 45) was generated. Sequence analysis and CDR analysis of the variable regions of the heavy chain and light chain of the S100A8/A9 monoclonal antibody (Clone No. 45) were performed, and a stable expression vector for CHO cells having incorporated therein sequences recombined with variable regions of human $IgG_2$ was generated and transduced into CHO cells in combination with a gene for the Fc portion of human $IgG_2$. Thus, the anti-S100A8/A9 chimeric antibody was stably generated (FIG. 15). The antibody was generated by a method described in WO 2017/061354 A1.

(Example 9) Lung Metastasis-Suppressing Effect in Tail Vein Injection of Mouse Melanoma B16-BL6 Cells Through use of a lung metastasis model of mouse melanoma B16-BL6 cells, the lung metastasis-suppressing effect of the anti-S100A8/A9 chimeric antibody generated in Example 8 was investigated.

Figure 16:
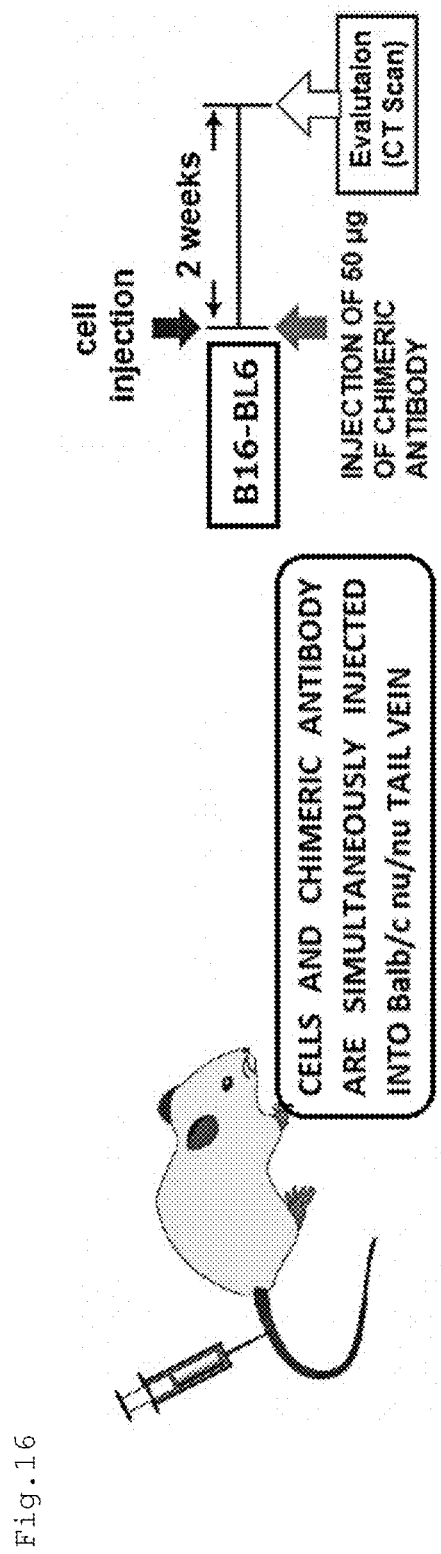
FIG. 16 is a diagram for illustrating a protocol for investigating the lung metastasis-suppressing effect of an anti-S100A8/A9 chimeric antibody (Chimeric-45) through use of a lung metastasis model of mouse melanoma B16-BL6 cells (Example 9).
Figure 17:
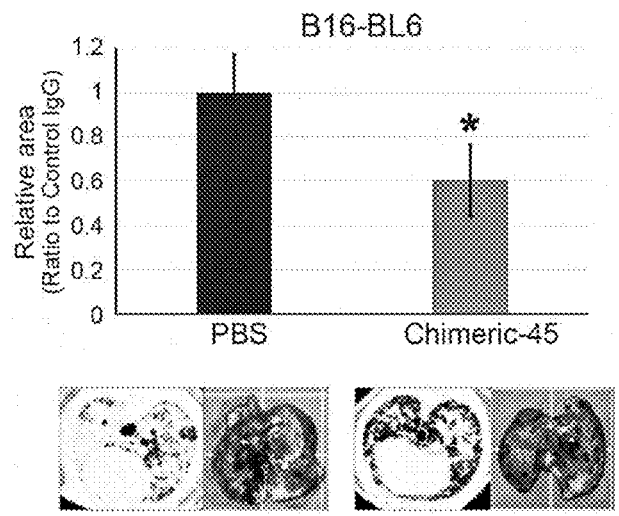
FIG. 17 includes a graph and images showing the results of a test according to the protocol illustrated in FIG. 16, wherein the results are typical lung and CT images in each CT scan and an area calculated from the CT image compared to those of a negative control group (Example 9).

In accordance with a protocol illustrated in FIG. 16, $1\times10^5$ mouse melanoma B16-BL6 cells and 50 μg of the anti-S100A8/A9 chimeric antibody were simultaneously injected into the tail vein of five Balb/c nu/nu mice per group, and 2 weeks later, CT scans were performed. FIG. 17 shows the results for comparing typical mouse lung and CT images and areas calculated from the CT images to those of a negative control group. As a result, it was recognized that the antibody of Clone No. 45 significantly suppressed lung metastasis also as the chimeric antibody obtained by fusing the Fc portion of human IgG2 thereto, demonstrating its usefulness as a lung metastasis suppressor for melanoma.

(Example 10) Lung Metastasis-Suppressing Effect in Local Injection of Mouse Melanoma B16-BL6 Cells In this Example, the lung metastasis-suppressing effect of the anti-S100A8/A9 monoclonal antibody (Clone No. 45) generated in Example 1 was investigated. In accordance with a protocol illustrated in FIG. 18, $1\times10^5$ mouse melanoma B16-BL6 cells were intradermally injected into the right ear of two Balb/c nu/nu mice per group. After a lapse of 13 days, at a time point when a tumor measuring from about 4 mm to about 5 mm was observed, 0 μg, 10 μg, 50 μg, or 100 μg of the anti-S100A8/A9 monoclonal antibody was injected into the tail vein. After 1 day from the antibody injection, the tumor in the right ear was partially resected to induce metastasis of the melanoma B16-BL6 cells. After a lapse of 20 days from the antibody injection, metastasis to the lungs was observed. As a result, it was observed that lung metastasis was suppressed in an injection concentration-dependent manner (FIG. 19). It was recognized that even antibody injection after tumor formation suppressed lung metastasis in a dose-dependent manner. In FIG. 19, "α-S100A8/A9 antibody (Ab45)" means the anti-S100A8/A9 monoclonal antibody (Clone No. 45).

Figure 18:
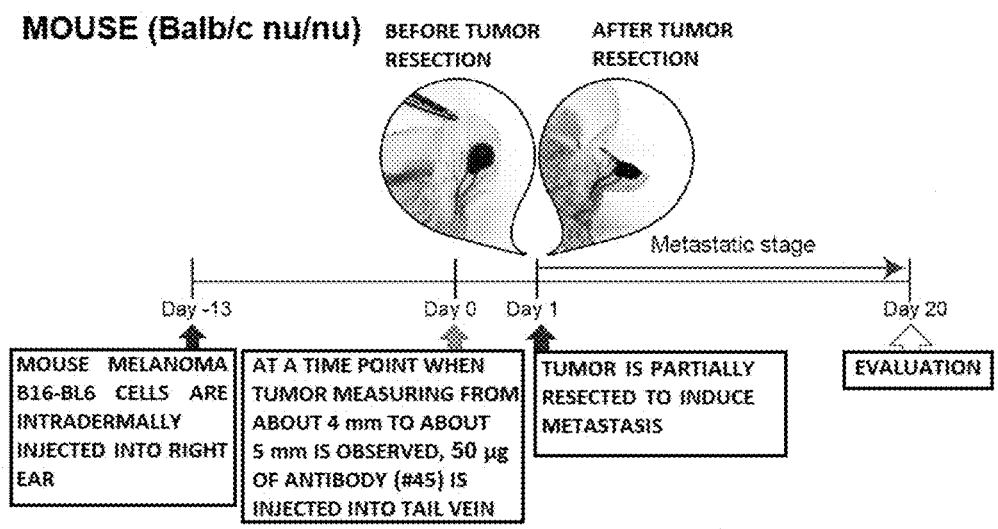
FIG. 18 is a diagram for illustrating a protocol for investigating the lung metastasis-suppressing effect of an anti-S100A8/A9 monoclonal antibody after the observation of a tumor caused by intradermal injection of mouse melanoma B16-BL6 into the right ear of each mice (Example 10).

In accordance with the protocol illustrated in FIG. 18, three Balb/c nu/nu mice per group were injected with 50 μg of the anti-S100A8/A9 monoclonal antibody (Clone No. 45) or IgG serving as a control, and after a lapse of 20 days, lung foci were checked. As a result, a metastasis-suppressing effect was clearly observed in the Clone No. 45-injected group (FIG. 20).

Lung foci were observed in each of the groups injected with 0 μg, 10 μg, 50 μg, and 100 μg of the anti-S100A8/A9 monoclonal antibody (Clone No. 45). As a result, in the 10 μg-injected group, a significant reduction in number of lung foci was found (Table 2). In Table 2 below, "α-S100A8/A9 antibody (Ab45)" means the anti-S100A8/A9 monoclonal antibody (Clone No. 45).

TABLE 2

| | | α-S100A8/A9 antibody (Ab45) | | | |
|---|---|---|---|---|---|
| | | 0 μg | 10 μg | 50 μg | 100 μg |
| The Number of Total Lung Foci (≥1 mm in diameter) | No. 1 | 22 | 13 | 2 | 1 |
| | No. 2 | 212 | 16 | 3 | 0 |

TABLE 2-continued

| | | α-S100A8/A9 antibody (Ab45) | | | |
|---|---|---|---|---|---|
| | | 0 μg | 10 μg | 50 μg | 100 μg |
| The Number of Lung Foci (≥5 mm in diameter) | No. 1 | 2 | 0 | 0 | 0 |
| | No. 2 | 0 | 0 | 0 | 0 |

Figure 21:
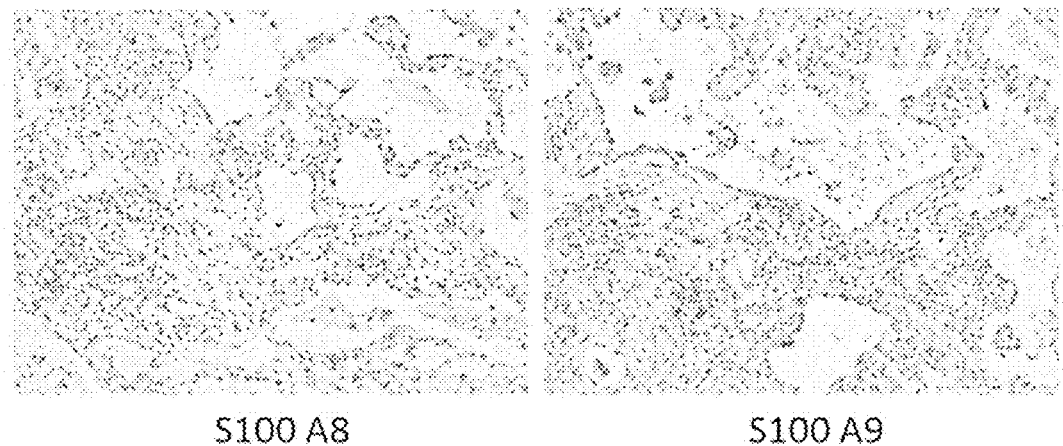
FIG. 21 includes immunohistochemical staining photographs showing the expressions of S100A8 and S100A9 in a lung tissue of an idiopathic pulmonary fibrosis patient (Example 11).
Figure 23:
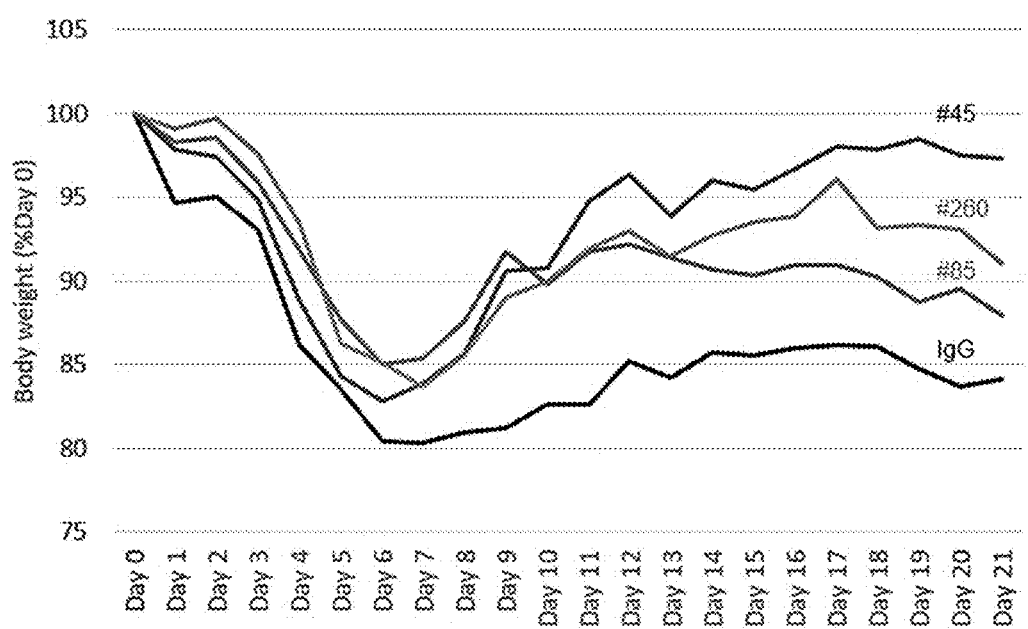
FIG. 23 is a graph showing results of a test according to the protocol illustrated in FIG. 21. The graph shows changes in body weight of the pulmonary fibrosis model mice intratracheally injected with bleomycin (Example 11).
Figure 22:
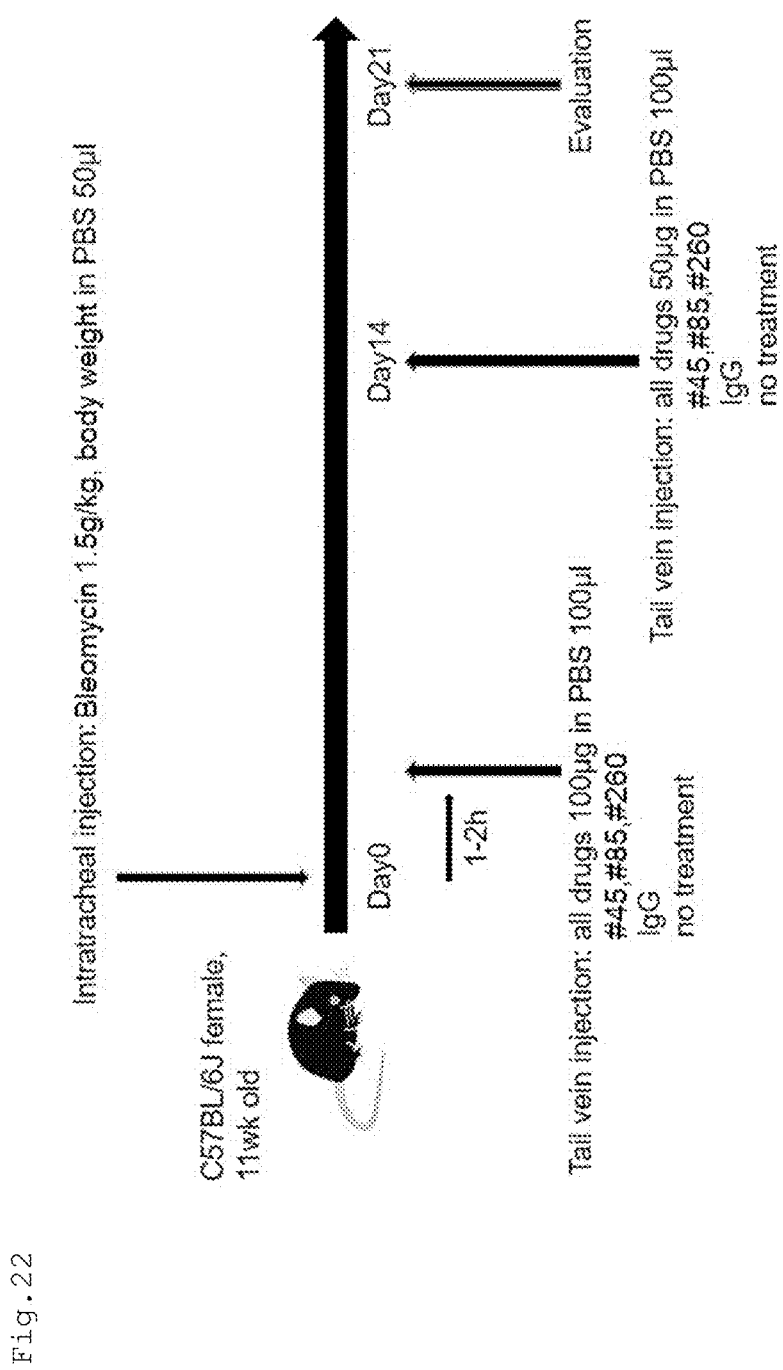
FIG. 22 is a diagram for illustrating a protocol for investigating the lung injury-suppressing effect of an anti-S100A8/A9 monoclonal antibody in pulmonary fibrosis model mice intratracheally injected with bleomycin (Example 11).
Figure 24:
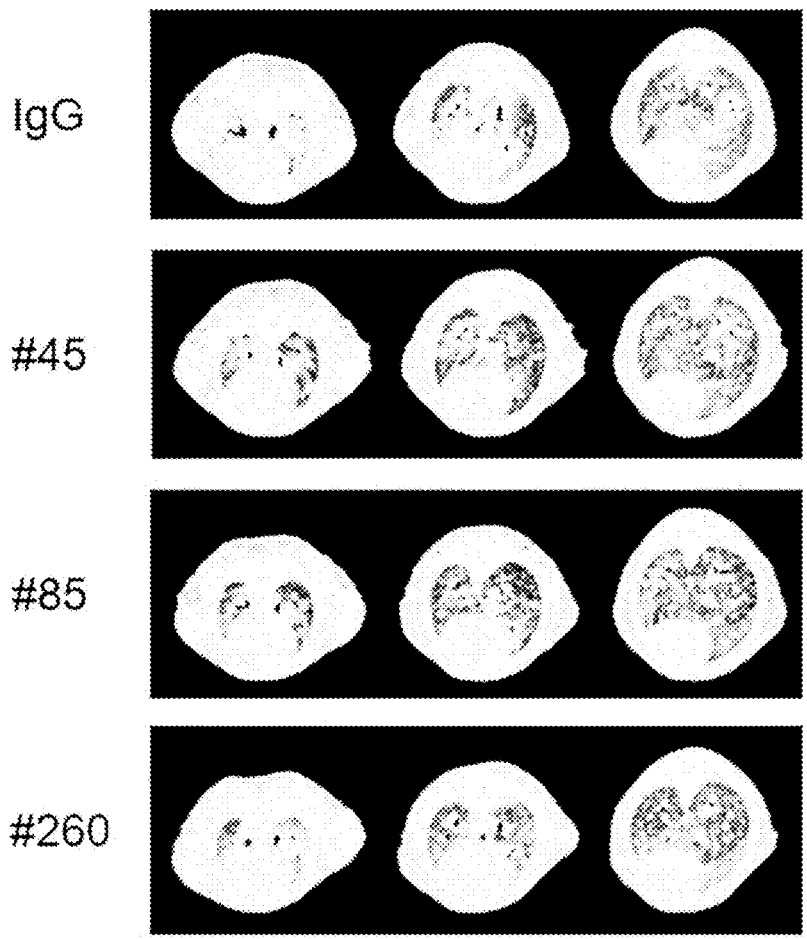
FIG. 24 shows results of the test according to the protocol illustrated in FIG. 21. The figure includes photographs showing typical lung and CT images in CT scans (Example 11).
Figure 25:
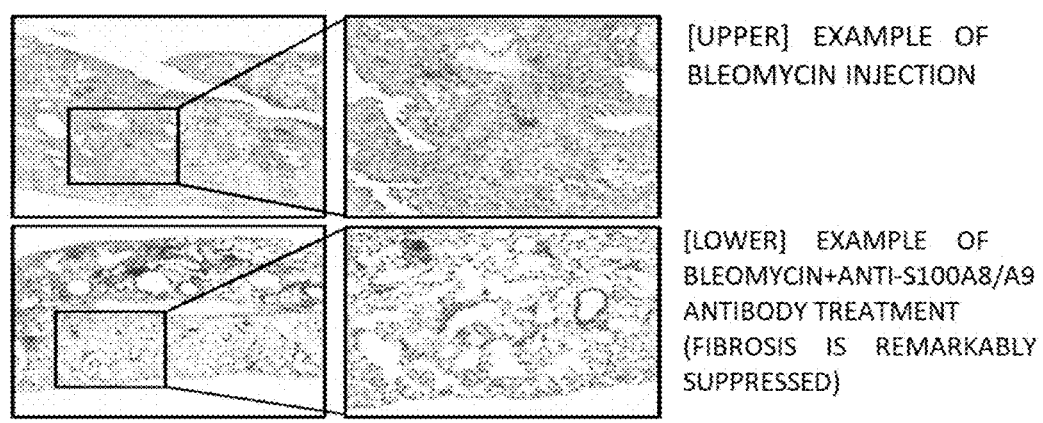
FIG. 25 shows results of the test according to the protocol illustrated in FIG. 21. The figure includes lung tissue photographs showing the ameliorating effect of the anti-S100A8/A9 monoclonal antibody in the pulmonary fibrosis model mice intratracheally injected with bleomycin (Example 11).

(Example 11) Lung Injury-Suppressing Effect in Pulmonary Fibrosis Model Intratracheally Injected with Bleomycin As shown in FIG. 21, it has been recognized that S100A8 and S100A9 proteins are expressed in a human lung tissue of idiopathic pulmonary fibrosis. In this Example, the lung injury-suppressing effect of the anti-S100A8/A9 monoclonal antibody (Clone No. 45) generated in Example 1 in a pulmonary fibrosis model intratracheally injected with bleomycin was investigated. In accordance with a protocol illustrated in FIG. 22, six or seven female C57BL/6J (11-week-old) mice per group were intratracheally injected with 50 μl of PBS containing 20 μg/mouse of bleomycin to generate acute lung injury model mice. As a result of the bleomycin injection, abrupt increases in S100A8 and S100A9, which are proteins involved in inflammation, were observed in the lung tissue (FIG. 22). At from 2 hours to 3 hours after the bleomycin injection, 50 μg of the anti-S100A8/A9 monoclonal antibody (Clone No. 45) was injected into the tail vein. As a control, IgG was injected. Changes in body weight of the acute lung injury model mice until a lapse of 21 days after the bleomycin injection were observed, and as a result, a mouse body weight reduction-suppressing effect was found in the anti-S100A8/A9 monoclonal antibody (Clone No. 45)-injected group as compared to the IgG-injected group (FIG. 23). Further, in the anti-S100A8/A9 monoclonal antibody (Clone No. 45)-injected group, a suppressing effect on lung injury on day 21 after the bleomycin injection was observed (FIG. 24). The lung injury was observed by CT scanning. As a result of an investigation by pathological observation of a tissue slice, a suppressing effect on the injury/fibrosis of the lung tissue was observed (FIG. 25).

Figure 26:
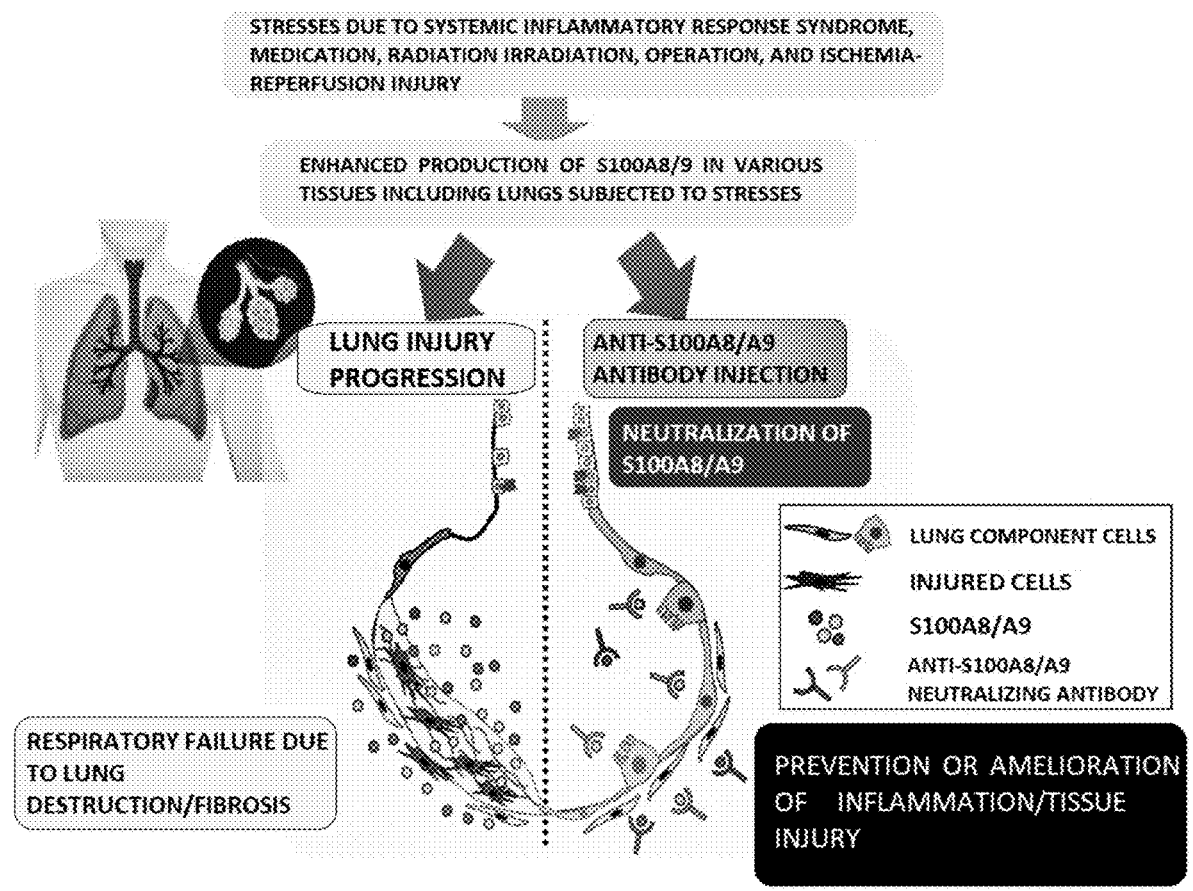
FIG. 26 is a diagram for schematically illustrating: a situation in which the production of S100A8/A9 is enhanced in the lungs of a patient subjected to various stresses due to, for example, systemic inflammatory response syndrome, medication, radiation irradiation, operation, and ischemic reperfusion injury, with the result that lung injury progresses; and the preventing or ameliorating effect of anti-S100A8/A9 antibody injection on the inflammation/tissue injury of the lung tissue (Example 11).

FIG. 26 is a schematic illustration of: a situation in which the production of S100A8 and S100A9 is enhanced in the lungs of a patient subjected to various stresses due to, for example, systemic inflammatory response syndrome, medication, radiation irradiation, operation, and ischemic reperfusion injury, with the result that lung injury progresses; and the preventing or ameliorating effect of anti-S100A8/A9 antibody injection on the inflammation/tissue injury of the lung tissue.

INDUSTRIAL APPLICABILITY

As described in detail above, the anti-S100A8/A9 antibody of the present invention has an action of suppressing the metastasis of cancer cells. In recent years, the survival rate of cancer patients has been presumably improved by virtue of improvements in, for example, prevention, diagnosis, and treatment of cancer. Also in anticancer agent treatment, effective treatment has been developed by, for example, using an anticancer agent having a high therapeutic effect and having reduced side effects, or combining a plurality of medicaments, to thereby improve a treatment outcome. However, there still remains a problem in that cancer metastasis is difficult to treat for the purpose of cure.

Under such circumstances, the anti-S100A8/A9 antibody of the present invention can effectively suppress the metastasis of cancer cells, thereby making a great contribution to improving a cancer treatment outcome, and hence the antibody is industrially extremely useful. Further, the anti-S100A8/A9 antibody of the present invention also takes effect on various inflammatory diseases, and hence the industrial usefulness of the present invention as such is immeasurable.

The invention claimed is:

1. A pharmaceutical composition, comprising an antibody or an antibody fragment thereof as an active ingredient, the antibody or the antibody fragment thereof having a neutralizing antibody affinity for a heterodimer of S100A8 and S100A9, and wherein said antibody or said antibody fragment thereof comprises a combination of:
a heavy chain variable region (VH CDR) comprising the amino acid sequence set forth in SEQ ID NO: 7, 8, and 9; and
(ii) a light chain variable region (VL CDR) comprising the amino acid sequence set forth in SEQ ID NO: 22, 23, and 24.

2. The pharmaceutical composition according to claim 1, wherein the antibody or the antibody fragment thereof has a neutralizing ability against the heterodimer of S100A8 and S100A9, and is free of reactivity to an S100A8 monomer and/or an S100A9 monomer.

3. The pharmaceutical composition according to claim 1, wherein the antibody or the antibody fragment thereof is a monoclonal antibody.

4. The pharmaceutical composition according to claim 3, wherein a subclass of the monoclonal antibody is selected from the group consisting of $IgG_1$, $IgG_2$, $IgG_3$, and $IgG_4$.

5. The pharmaceutical composition according to claim 1, wherein the antibody or the antibody fragment thereof comprises:
heavy chain variable regions comprising a heavy chain variable region 1 (CDR H1), a heavy chain variable region 2 (CDR H2), and a heavy chain variable region 3 (CDR H3); and
light chain variable regions comprising a light chain variable region 1 (CDR L1), a light chain variable region 2 (CDR L2), and a light chain variable region 3 (CDR L3), wherein the heavy chain variable region 1 (CDR H1) comprises the amino acid sequence set forth in SEQ ID NO: 7,
wherein the heavy chain variable region 2 (CDR H2) comprises the amino acid sequence set forth in SEQ ID NO: 8,
wherein the heavy chain variable region 3 (CDR H3) comprises the amino acid sequence set forth in SEQ ID NO: 9,
wherein the light chain variable region 1 (CDR L1) comprises the amino acid sequence set forth in SEQ ID NO: 22,
wherein the light chain variable region 2 (CDR L2) comprises the amino acid sequence set forth in SEQ ID NO: 23,
wherein the light chain variable region 3 (CDR L3) comprises the amino acid sequence set forth in SEQ ID NO: 24.

6. The pharmaceutical composition according to claim 1, wherein said antibody or said antibody fragment thereof is an anticancer agent, an anti-inflammatory agent, or a combination thereof.

7. The pharmaceutical composition according to claim 6, wherein the anticancer agent is a cancer metastasis suppressor and/or a cancer therapeutic agent.

8. The pharmaceutical composition according to claim 6, wherein said anticancer agent is used to treat a cancer selected from the group consisting of skin cancer, lung cancer, stomach cancer, colon cancer, pancreatic cancer, liver cancer, lung cancer, kidney cancer, breast cancer, uterine cancer, bile duct cancer, esophageal cancer, pharyngeal cancer, biliary tract cancer, bladder cancer, blood cancer, lymphoma, ovarian cancer, prostate cancer, brain tumor, thyroid cancer, and a combination thereof.

9. An isolated antibody or an antibody fragment thereof comprising a combination of:
   (i) heavy chain variable region (VH CDR) comprising the amino acid sequences set forth in SEQ ID NO: 7, 8, and 9; and
   (ii) a light chain variable region (VL CDR) comprising the amino acid sequences set forth in SEQ ID NO: 22, 23, and 24,
wherein said isolated antibody or said antibody fragment thereof has a neutralizing antibody affinity for a heterodimer of S100A8 and S100A9.

10. The isolated antibody or antibody fragment thereof according to claim 9, wherein the antibody or the antibody fragment thereof has a neutralizing ability against the heterodimer of S100A8 and S100A9, and is free of reactivity to an S100A8 monomer and/or an S100A9 monomer.

11. The isolated antibody or antibody fragment thereof according to claim 9, wherein the antibody or the antibody fragment thereof is a monoclonal antibody.

12. The isolated antibody or antibody fragment thereof according to claim 11, wherein a subclass of the monoclonal antibody is selected from the group consisting of $IgG_1$, $IgG_2$, $IgG_3$, and $IgG_4$.

13. The isolated antibody or antibody fragment thereof according to claim 11 comprising:
   heavy chain variable regions comprising a heavy chain variable region 1 (CDR H1), a heavy chain variable region 2 (CDR H2), and a heavy chain variable region 3 (CDR H3); and
   light chain variable regions comprising a light chain variable region 1 (CDR L1), a light chain variable region 2 (CDR L2), and a light chain variable region 3 (CDR L3).

14. The isolated antibody or antibody fragment thereof according to claim 13, wherein the heavy chain variable region 1 (CDR H1) comprises the amino acid sequence set forth in SEQ ID NO: 7.

15. The isolated antibody or antibody fragment thereof according to claim 13, wherein the heavy chain variable region 2 (CDR H2) comprises the amino acid sequence set forth in SEQ ID NO: 8.

16. The isolated antibody or antibody fragment thereof according to claim 13, wherein the heavy chain variable region 3 (CDR H3) comprises the amino acid sequence set forth in SEQ ID NO: 9.

17. The isolated antibody or antibody fragment thereof according to claim 13, wherein the light chain variable region 1 (CDR L1) comprises the amino acid sequence set forth in SEQ ID NO: 22.

18. The isolated antibody or antibody fragment thereof according to claim 13, wherein the light chain variable region 2 (CDR L2) comprises the amino acid sequence set forth in SEQ ID NO: 23.

19. The isolated antibody or antibody fragment thereof according to claim 13, wherein the light chain variable region 3 (CDR L3) comprises the amino acid sequence set forth in SEQ ID NO: 24.

20. The isolated antibody or the antibody fragment thereof of claim 9, wherein said antibody has a neutralizing antibody affinity for a heterodimer of S100A8 and S100A9, the neutralizing antibody affinity being higher than a neutralizing antibody affinity of the antibody or the antibody fragment thereof for an S100A8 monomer.

* * * * *

SEQUENCE LISTING

<160> NUMBER OF SEQ ID NOS: 36

<210> SEQ ID NO 1
<211> LENGTH: 20
<212> TYPE: DNA
<213> ORGANISM: Artificial
<220> FEATURE:
<223> OTHER INFORMATION: Fwd primer for TNF alpha

<400> SEQUENCE: 1
gacaagcctg tagcccatgt     20

<210> SEQ ID NO 2
<211> LENGTH: 18
<212> TYPE: DNA
<213> ORGANISM: Artificial
<220> FEATURE:
<223> OTHER INFORMATION: Rev primer for TNF alpha

<400> SEQUENCE: 2
tctcagctcc acgccatt     18

<210> SEQ ID NO 3
<211> LENGTH: 18
<212> TYPE: DNA
<213> ORGANISM: Artificial

```
<220> FEATURE:
<223> OTHER INFORMATION: Fwd primer for IL-6

<400> SEQUENCE: 3
cttccctgcc ccagtacc                                                 18

<210> SEQ ID NO 4
<211> LENGTH: 21
<212> TYPE: DNA
<213> ORGANISM: Artificial
<220> FEATURE:
<223> OTHER INFORMATION: Rev primer for IL-6

<400> SEQUENCE: 4
ctgaagaggt gagtggctgt c                                             21

<210> SEQ ID NO 5
<211> LENGTH: 20
<212> TYPE: DNA
<213> ORGANISM: Artificial
<220> FEATURE:
<223> OTHER INFORMATION: Fwd primer for IL-8

<400> SEQUENCE: 5
agacagcaga gcacacaagc                                               20

<210> SEQ ID NO 6
<211> LENGTH: 19
<212> TYPE: DNA
<213> ORGANISM: Artificial
<220> FEATURE:
<223> OTHER INFORMATION: Rev primer for IL-8

<400> SEQUENCE: 6
aggaaggctg ccaagagag                                                19

<210> SEQ ID NO 7
<211> LENGTH: 5
<212> TYPE: PRT
<213> ORGANISM: Artificial
<220> FEATURE:
<223> OTHER INFORMATION: No.45:CDR H1

<400> SEQUENCE: 7

Ser Tyr Trp Met Gln
1               5

<210> SEQ ID NO 8
<211> LENGTH: 17
<212> TYPE: PRT
<213> ORGANISM: Artificial
<220> FEATURE:
<223> OTHER INFORMATION: No.45:CDR H2

<400> SEQUENCE: 8

Ala Ile Tyr Pro Gly Asp Gly Asp Thr Arg Asp Thr Gln Lys Phe Lys
1               5                   10                  15

Gly

<210> SEQ ID NO 9
<211> LENGTH: 10
<212> TYPE: PRT
<213> ORGANISM: Artificial
<220> FEATURE:
<223> OTHER INFORMATION: No.45:CDR H3
```

```
<400> SEQUENCE: 9

Met Ala Gly Tyr Asn Tyr Asp Asn Asp Tyr
1               5                   10

<210> SEQ ID NO 10
<211> LENGTH: 6
<212> TYPE: PRT
<213> ORGANISM: Artificial
<220> FEATURE:
<223> OTHER INFORMATION: No.85:CDR H1

<400> SEQUENCE: 10

Ser Gly Tyr Asn Trp His
1               5

<210> SEQ ID NO 11
<211> LENGTH: 16
<212> TYPE: PRT
<213> ORGANISM: Artificial
<220> FEATURE:
<223> OTHER INFORMATION: No.85:CDR H2

<400> SEQUENCE: 11

Tyr Ile Gln Tyr Ser Gly Ser Thr Asn Tyr Asn Pro Ser Leu Lys Ser
1               5                   10                  15

<210> SEQ ID NO 12
<211> LENGTH: 11
<212> TYPE: PRT
<213> ORGANISM: Artificial
<220> FEATURE:
<223> OTHER INFORMATION: No.85:CDR H3

<400> SEQUENCE: 12

Ala Leu Arg Tyr Asp Tyr Ser Trp Phe Ala Tyr
1               5                   10

<210> SEQ ID NO 13
<211> LENGTH: 5
<212> TYPE: PRT
<213> ORGANISM: Artificial
<220> FEATURE:
<223> OTHER INFORMATION: No.235:CDR H1

<400> SEQUENCE: 13

Asn Phe Trp Met Asn
1               5

<210> SEQ ID NO 14
<211> LENGTH: 17
<212> TYPE: PRT
<213> ORGANISM: Artificial
<220> FEATURE:
<223> OTHER INFORMATION: No.235:CDR H2

<400> SEQUENCE: 14

Gln Ile Tyr Pro Gly Lys Ser Asp Thr Asn Tyr Asn Gly Lys Phe Lys
1               5                   10                  15

Gly

<210> SEQ ID NO 15
<211> LENGTH: 14
<212> TYPE: PRT
<213> ORGANISM: Artificial
<220> FEATURE:
<223> OTHER INFORMATION: No.235:CDR H3
```

```
<400> SEQUENCE: 15

Trp Gly Ala Tyr Tyr Lys Tyr Gly Gly Ser Tyr Phe Asp Tyr
1               5                   10

<210> SEQ ID NO 16
<211> LENGTH: 7
<212> TYPE: PRT
<213> ORGANISM: Artificial
<220> FEATURE:
<223> OTHER INFORMATION: No.258:CDR H1

<400> SEQUENCE: 16

Thr Ala Ser Met Gly Val Ser
1               5

<210> SEQ ID NO 17
<211> LENGTH: 16
<212> TYPE: PRT
<213> ORGANISM: Artificial
<220> FEATURE:
<223> OTHER INFORMATION: No.258:CDR H2

<400> SEQUENCE: 17

His Ile Tyr Trp Asp Asp Asp Lys Arg Tyr Asn Pro Ser Leu Lys Ser
1               5                   10                  15

<210> SEQ ID NO 18
<211> LENGTH: 8
<212> TYPE: PRT
<213> ORGANISM: Artificial
<220> FEATURE:
<223> OTHER INFORMATION: No.258:CDR H3

<400> SEQUENCE: 18

Arg Pro Leu Gly Tyr Phe Asp Val
1               5

<210> SEQ ID NO 19
<211> LENGTH: 5
<212> TYPE: PRT
<213> ORGANISM: Artificial
<220> FEATURE:
<223> OTHER INFORMATION: No.260:CDR H1

<400> SEQUENCE: 19

Asn Tyr Gly Val His
1               5

<210> SEQ ID NO 20
<211> LENGTH: 16
<212> TYPE: PRT
<213> ORGANISM: Artificial
<220> FEATURE:
<223> OTHER INFORMATION: No.260:CDR H2

<400> SEQUENCE: 20

Val Val Trp Ala Gly Gly Ser Thr Asn Tyr Asn Ser Ala Leu Met Ser
1               5                   10                  15

<210> SEQ ID NO 21
<211> LENGTH: 13
<212> TYPE: PRT
<213> ORGANISM: Artificial
<220> FEATURE:
<223> OTHER INFORMATION: No.260:CDR H3
```

```
<400> SEQUENCE: 21

Ala Arg Asp Tyr Tyr Gly Tyr Asp Gly Tyr Phe Gly Ala
1               5                   10

<210> SEQ ID NO 22
<211> LENGTH: 11
<212> TYPE: PRT
<213> ORGANISM: Artificial
<220> FEATURE:
<223> OTHER INFORMATION: No.45: CDR L1

<400> SEQUENCE: 22

Lys Ala Ser Gln Asp Ile Asn Lys Tyr Ile Ala
1               5                   10

<210> SEQ ID NO 23
<211> LENGTH: 7
<212> TYPE: PRT
<213> ORGANISM: Artificial
<220> FEATURE:
<223> OTHER INFORMATION: No.45: CDR L2

<400> SEQUENCE: 23

Tyr Thr Ser Thr Leu Gln Pro
1               5

<210> SEQ ID NO 24
<211> LENGTH: 8
<212> TYPE: PRT
<213> ORGANISM: Artificial
<220> FEATURE:
<223> OTHER INFORMATION: No.45: CDR L3

<400> SEQUENCE: 24

Leu Gln Tyr Asp Asn Leu Arg Thr
1               5

<210> SEQ ID NO 25
<211> LENGTH: 11
<212> TYPE: PRT
<213> ORGANISM: Artificial
<220> FEATURE:
<223> OTHER INFORMATION: No.85: CDR L1

<400> SEQUENCE: 25

Lys Ala Ser Gln Asp Val Ser Thr Ala Val Ala
1               5                   10

<210> SEQ ID NO 26
<211> LENGTH: 7
<212> TYPE: PRT
<213> ORGANISM: Artificial
<220> FEATURE:
<223> OTHER INFORMATION: No.85: CDR L2

<400> SEQUENCE: 26

Ser Ala Ser Tyr Arg Tyr Thr
1               5

<210> SEQ ID NO 27
<211> LENGTH: 9
<212> TYPE: PRT
<213> ORGANISM: Artificial
<220> FEATURE:
<223> OTHER INFORMATION: No.85: CDR L3

<400> SEQUENCE: 27
```

```
Gln Gln His Tyr Ser Thr Pro Leu Thr
1               5

<210> SEQ ID NO 28
<211> LENGTH: 11
<212> TYPE: PRT
<213> ORGANISM: Artificial
<220> FEATURE:
<223> OTHER INFORMATION: No.235: CDR L1

<400> SEQUENCE: 28

Ser Ala Ser Gln Gly Ile Ser Asn Tyr Leu Asn
1               5                   10

<210> SEQ ID NO 29
<211> LENGTH: 7
<212> TYPE: PRT
<213> ORGANISM: Artificial
<220> FEATURE:
<223> OTHER INFORMATION: No.235: CDR L2

<400> SEQUENCE: 29

Tyr Thr Ser Ser Leu His Ser
1               5

<210> SEQ ID NO 30
<211> LENGTH: 9
<212> TYPE: PRT
<213> ORGANISM: Artificial
<220> FEATURE:
<223> OTHER INFORMATION: No.235: CDR L3

<400> SEQUENCE: 30

Gln Gln Tyr Ser Lys Phe Pro Tyr Thr
1               5

<210> SEQ ID NO 31
<211> LENGTH: 11
<212> TYPE: PRT
<213> ORGANISM: Artificial
<220> FEATURE:
<223> OTHER INFORMATION: No.258: CDR L1

<400> SEQUENCE: 31

Lys Ala Ser Gln Asp Ile Asn Asn Tyr Ile Ser
1               5                   10

<210> SEQ ID NO 32
<211> LENGTH: 7
<212> TYPE: PRT
<213> ORGANISM: Artificial
<220> FEATURE:
<223> OTHER INFORMATION: No.258: CDR L2

<400> SEQUENCE: 32

Tyr Thr Ser Thr Leu Gln Pro
1               5

<210> SEQ ID NO 33
<211> LENGTH: 9
<212> TYPE: PRT
<213> ORGANISM: Artificial
<220> FEATURE:
<223> OTHER INFORMATION: No.258: CDR L3

<400> SEQUENCE: 33
```

```
Leu Gln Tyr Asp Asn Leu Leu Trp Thr
1               5

<210> SEQ ID NO 34
<211> LENGTH: 11
<212> TYPE: PRT
<213> ORGANISM: Artificial
<220> FEATURE:
<223> OTHER INFORMATION: No.260: CDR L1

<400> SEQUENCE: 34

Lys Ala Ser Gln Asp Ile Asn Ser Tyr Leu Thr
1               5                   10

<210> SEQ ID NO 35
<211> LENGTH: 7
<212> TYPE: PRT
<213> ORGANISM: Artificial
<220> FEATURE:
<223> OTHER INFORMATION: No.260: CDR L2

<400> SEQUENCE: 35

Arg Ala Asn Arg Leu Val Asp
1               5

<210> SEQ ID NO 36
<211> LENGTH: 9
<212> TYPE: PRT
<213> ORGANISM: Artificial
<220> FEATURE:
<223> OTHER INFORMATION: No.260: CDR L3

<400> SEQUENCE: 36

Leu Gln Tyr Asp Glu Phe Pro Leu Thr
1               5
```